US012613247B2

(12) United States Patent
Le Bihan et al.

(10) Patent No.: US 12,613,247 B2
(45) Date of Patent: Apr. 28, 2026

(54) LABELLING METHOD TO DISTINGUISH ISOBARIC AMINO ACIDS AND AMINO ACID COMBINATIONS

(71) Applicant: RAPID NOVOR INC., Kitchener (CA)

(72) Inventors: Thierry Le Bihan, Kitchener (CA); Bin Ma, Kitchener (CA); Zac McDonald, Kitchener (CA); Qixin Liu, Kitchener (CA); Paul Taylor, Kitchener (CA)

(73) Assignee: RAPID NOVOR INC., Kitchener (CA)

( * ) Notice: Subject to any disclaimer, the term of this patent is extended or adjusted under 35 U.S.C. 154(b) by 156 days.

(21) Appl. No.: 17/414,245

(22) PCT Filed: Dec. 19, 2019

(86) PCT No.: PCT/CA2019/051870
§ 371 (c)(1),
(2) Date: Jun. 15, 2021

(87) PCT Pub. No.: WO2020/124242
PCT Pub. Date: Jun. 25, 2020

(65) Prior Publication Data
US 2022/0026438 A1     Jan. 27, 2022

Related U.S. Application Data

(60) Provisional application No. 62/783,026, filed on Dec. 20, 2018.

(51) Int. Cl.
| | |
|---|---|
| *G01N 33/68* | (2006.01) |
| *C07K 1/10* | (2006.01) |
| *C07K 1/107* | (2006.01) |
| *C07K 1/14* | (2006.01) |
| *C07K 1/20* | (2006.01) |
| *G01N 1/40* | (2006.01) |

(52) U.S. Cl.
CPC ........... *G01N 33/6812* (2013.01); *C07K 1/10* (2013.01); *C07K 1/1072* (2013.01); *C07K 1/145* (2013.01); *C07K 1/20* (2013.01); *G01N 1/4044* (2013.01)

(58) Field of Classification Search
None
See application file for complete search history.

(56) References Cited

U.S. PATENT DOCUMENTS 7,294,707 B2 * 11/2007 Nakazawa ............. C07K 1/003
530/402

FOREIGN PATENT DOCUMENTS

| CN | 1556925 A | 12/2004 |
|---|---|---|
| CN | 1749269 A | 5/2006 |

OTHER PUBLICATIONS

Subirós-Funosas, R., et al. 2009 Chem Eur J 15: 9394-9403. (Year: 2009).*
Yeung, Y-G., et al. 2010 Current Protocols in Protein Science 16.12.1-16.12.5: 5 pages. (Year: 2010).*
Extended European Search Report for EP19905526.5, mailed Oct. 12, 2022.
Samgina et al., "EThcD Discrimination of Isomeric Leucine/Isoleucine Residues in Sequencing of the Intact Skin Frog Peptides with Intramolecular Disulfide Bond," J. Am. Soc. Mass Spectrom. 29:842-852 (2017).
Xiao et al., "Distinguishing between Leucine and Isoleucine by Integrated LC-MS Analysis Using an Orbitrap Fusion Mass Spectrometer," Anal. Chem. 88:10757-10766 (2016).
Frey et al., "Chemical Derivatization of Peptide Carboxyl Groups for Highly Efficient Electron Transfer Dissociation," J. Am. Soc. Mass Spectrom. 24:1710-1721 (2013).
Somasundaram et al., "C-Terminal Charge-Reversal Derivatization and Parallel Use of Multiple Proteases Facilitates Identification of Protein C-Termini by C-Terminomics," J. Proteome Res. 15:1369-1378 (2016).
Ko et al., "Enhanced Electron Transfer Dissociation of Peptides Edified at C-terminus with Fixed Charges," J. Am. Soc. Mass Spectrom. 23:1991-2000 (2012).
International Search Report and Written Opinion for corresponding Application No. PCT/CA2019/051870 (mailed Mar. 26, 2020).
Zhokhov et al., "An ETheD-Based Method for Discrimination of Leucine and Isoleucine Residues in Tryptic Peptides," J. Am. Soc. Mass Spectrometry 28(8):1600-1611 (2017).
Watson et al., "Characterization of the Ethyl-Triphenylphosphonium Derivative of Model Peptides by Fast Atom Bombardment Collisionally-Activated Dissociation Tandem Mass Spectrometry Using B/E Linked Scans," Internat. J. Mass Spectrometry Ion Proc. 111:191-209 (1991).
Zaia et al., "Comparison of Charged Derivatives for High Energy Collision-Induced Dissociation Tandem Mass Spectrometry," J. Am. Soc. Mass Spectrometry 6(5):428-436 (1995).
Examination Report in CN 201980084538.6 (dated Dec. 6, 2023).

* cited by examiner

*Primary Examiner* — Marsha Tsay
(74) *Attorney, Agent, or Firm* — Troutman Pepper Locke LLP (Rochester)

(57) ABSTRACT

A method for increasing peptide fragmentation by labelling the peptide at the C-terminal end with a guanidinium group or other basic functional group and distinguishing isobaric amino acids and amino acid combinations of asparagine and glycine-glycine; glutamine and glycine-alanine; and/or glutamine and alanine-glycine, during polypeptide sequencing. The method involves: obtaining a peptide of interest and/or digesting a polypeptide of interest with a protease, such as pepsin, chymotrypsin or trypsin, or by chemical cleavage to produce shorter peptides; reacting the obtained and/or generated peptides with a coupling reagent to derivatize the free C-terminal carboxylic acid function of the peptides, thus adding a basic functional group rendering C-terminal peptide fragment ions detectable by mass spectrometry; selecting a charge state of 2+ or more, and fragmenting the derivatized peptides in a mass spectrometer under conditions effective to generate at least w ions; and detecting the w ions by mass spectrometry, and identifying derivatized peptides which incorporate the additional mass of the basic functional group.

20 Claims, 18 Drawing Sheets

Specification includes a Sequence Listing.

SEQUENCE LISTING

```
<160> NUMBER OF SEQ ID NOS: 18

<210> SEQ ID NO 1
<211> LENGTH: 14
<212> TYPE: PRT
<213> ORGANISM: Artificial Sequence
<220> FEATURE:
<223> OTHER INFORMATION: peptide

<400> SEQUENCE: 1

Phe Asp Lys Leu Lys His Leu Val Asp Glu Pro Gln Asn Leu
1               5                   10

<210> SEQ ID NO 2
<211> LENGTH: 16
<212> TYPE: PRT
<213> ORGANISM: Artificial Sequence
<220> FEATURE:
<223> OTHER INFORMATION: peptide

<400> SEQUENCE: 2

Ala Val Glu Gly Pro Lys Leu Val Val Ser Thr Gln Thr Ala Leu Ala
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: peptide

<400> SEQUENCE: 3

Asp Glu His Val Lys Leu Val Asn Glu Leu Thr Glu Phe
1               5                   10

<210> SEQ ID NO 4
<211> LENGTH: 13
<212> TYPE: PRT
<213> ORGANISM: Artificial Sequence
```

```
<220> FEATURE:
<223> OTHER INFORMATION: peptide

<400> SEQUENCE: 4

Gln Glu Ala Lys Asp Ala Phe Leu Gly Ser Phe Leu Tyr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: peptide

<400> SEQUENCE: 5

Phe Glu Lys Leu Gly Glu Tyr Gly Phe Gln Asn Ala Leu
1               5                   10

<210> SEQ ID NO 6
<211> LENGTH: 8
<212> TYPE: PRT
<213> ORGANISM: Artificial Sequence
<220> FEATURE:
<223> OTHER INFORMATION: peptide

<400> SEQUENCE: 6

Leu Gln Gln Cys Pro Phe Asp Glu
1               5

<210> SEQ ID NO 7
<211> LENGTH: 5
<212> TYPE: PRT
<213> ORGANISM: Artificial Sequence
<220> FEATURE:
<223> OTHER INFORMATION: peptide

<400> SEQUENCE: 7

Tyr Gly Gly Phe Leu
1               5

<210> SEQ ID NO 8
<211> LENGTH: 6
<212> TYPE: PRT
<213> ORGANISM: Artificial Sequence
<220> FEATURE:
<223> OTHER INFORMATION: peptide

<400> SEQUENCE: 8

Gly Val Ile Ala Ser Thr
1               5

<210> SEQ ID NO 9
<211> LENGTH: 6
<212> TYPE: PRT
<213> ORGANISM: Artificial Sequence
<220> FEATURE:
<223> OTHER INFORMATION: peptide

<400> SEQUENCE: 9

Gly Val Leu Ala Ser Thr
1               5

<210> SEQ ID NO 10
<211> LENGTH: 7
<212> TYPE: PRT
<213> ORGANISM: Artificial Sequence
<220> FEATURE:
```

-continued

```
<223> OTHER INFORMATION: peptide
<220> FEATURE:
<221> NAME/KEY: misc_feature
<222> LOCATION: (7)..(7)
<223> OTHER INFORMATION: Xaa is arginine-methyl ester

<400> SEQUENCE: 10

Tyr Gly Gly Phe Leu Arg Xaa
1               5

<210> SEQ ID NO 11
<211> LENGTH: 17
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (17)..(17)
<223> OTHER INFORMATION: Xaa is MetArg

<400> SEQUENCE: 11

Ala Val Glu Gly Pro Lys Leu Val Val Ser Thr Gln Thr Ala Leu Ala
1               5                   10                  15

Xaa

<210> SEQ ID NO 12
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (14)..(14)
<223> OTHER INFORMATION: Xaa is MetArg

<400> SEQUENCE: 12

Asp Glu His Val Lys Leu Val Asn Glu Leu Thr Glu Phe Xaa
1               5                   10

<210> SEQ ID NO 13
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (14)..(14)
<223> OTHER INFORMATION: Xaa is MetArg

<400> SEQUENCE: 13

Gln Glu Ala Lys Asp Ala Phe Leu Gly Ser Phe Leu Tyr Xaa
1               5                   10

<210> SEQ ID NO 14
<211> LENGTH: 14
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (14)..(14)
<223> OTHER INFORMATION: Xaa is MetArg

<400> SEQUENCE: 14

Phe Glu Lys Leu Gly Glu Tyr Gly Phe Gln Asn Ala Leu Xaa
```

-continued

```
1               5               10
```

```
<210> SEQ ID NO 15
<211> LENGTH: 9
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (9)..(9)
<223> OTHER INFORMATION: Xaa is 3DMP

<400> SEQUENCE: 15

Leu Gln Gln Cys Pro Phe Asp Glu Xaa
1               5

<210> SEQ ID NO 16
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (7)..(7)
<223> OTHER INFORMATION: Xaa is MetArg

<400> SEQUENCE: 16

Gly Val Leu Ala Ser Thr Xaa
1               5

<210> SEQ ID NO 17
<211> LENGTH: 7
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (7)..(7)
<223> OTHER INFORMATION: Xaa is MetArg

<400> SEQUENCE: 17

Gly Val Ile Ala Ser Thr Xaa
1               5

<210> SEQ ID NO 18
<211> LENGTH: 15
<212> TYPE: PRT
<213> ORGANISM: Artificial Sequence
<220> FEATURE:
<223> OTHER INFORMATION: peptide
<220> FEATURE:
<221> NAME/KEY: misc_feature
<222> LOCATION: (15)..(15)
<223> OTHER INFORMATION: Xaa is MetArg

<400> SEQUENCE: 18

Phe Asp Lys Leu Lys His Leu Val Asp Glu Pro Gln Asn Leu Xaa
1               5               10              15
```

LABELLING METHOD TO DISTINGUISH ISOBARIC AMINO ACIDS AND AMINO ACID COMBINATIONS

This application is a national stage application under 35 U.S.C. § 371 of PCT Application No. PCT/CA2019/051870, filed Dec. 19, 2019, which claims the priority benefit of U.S. Provisional Patent Application Ser. No. 62/783,026, filed Dec. 20, 2018.

FIELD OF INVENTION

The present invention relates to polypeptide sequencing methods. In particular, the invention relates to methods for distinguishing isobaric amino acids and amino acid combinations of asparagine and glycine-glycine; glutamine and glycine-alanine; and/or glutamine and alanine-glycine, during polypeptide sequencing.

BACKGROUND OF THE INVENTION

Mass spectrometry has been used for decades for peptide sequencing. Typically, a given peptide is isolated and fragmented. Under low collision energy, peptide fragmentation occurs at the peptide bond or in its vicinity. The fragments ions including the peptide's N-terminus are named a, b or c ions depending on the exact location of the fragmentation pattern, and their respective complementary fragments from the C-terminal end are named x, y or z, respectively. A y1 ion will refer to the first amino acid residues on the C-terminal side, while b 1 will refer to the first amino acid residues on the N-terminal side of the peptide; a y3 ion will be an ion composed of the last 3 amino acids on the C-terminal side of a peptide and is complemented by a b ion b (n−3) where "n" is the number of amino acid residues in the specific peptide. Using EThcD (Electron Transfer Dissociation higher energy collision induced Dissociation) allows the generation of additional types of ions which are associated to side-chain cleavage (d and w ions) (Wysocki et al 2005; Johnson et al 1988; Frese et al 2012).

Trypsin is a protease that cleaves proteins into shorter peptides, which are generally easier to be analyzed and sequenced by mass spectrometry. An advantage of using trypsin instead of any other proteases is that both ends of a peptide resulting from the action of trypsin will typically carry a positive charge, thus upon MS/MS fragmentation, both end fragments are usually detectable by mass spectrometry. Under acidic conditions (normally between pH 2 to 4 for MS analysis), the peptide N-terminus is protonated (pKa of 8.2) and similarly the C-terminus end is also protonated either from a K (Lysine, pKa of 9.74) or R (Arginine, pKa of 10.76) sidechain, which are the 2 cleavage sites of trypsin. Using pepsin digestion, N-terminal fragment ions will be detectable but regarding the C-terminal fragments, only fragment ions including a K or R will most likely be detectable. C-terminal fragments, resulting from a protease other than trypsin or lys-C are often not detected due to their poor ionization state. FIG. 1 illustrates protein cleavage generated from the action of trypsin versus pepsin and which fragments can be used in MS/MS sequencing. The green bar shows peptides that should ionized, thus being detectable by the mass spectrometer. Most of the fragments from the N-terminal peptide, independently of which protease is used, should be ionized (shown by the green bar on the right side of each digest). On the other end, peptide fragments from the C-terminal end of the peptide will only be detected if they contain one of the basic residues (K, R or H). The bar in red on the right side of FIG. 1 illustrates C-terminal peptide fragments not containing any basic residues and that are therefore not often detectable by the mass spectrometer.

Assigning a sequence from a mass/charge peptide profile is based on measuring the mass difference between fragment ions, as most amino acid residues have different masses with the exception of two amino acids that have the exact same masses (classified as true isobaric): Leucine and Isoleucine. Since they have exactly the same mass and chemical composition, they cannot be easily assigned in a sequence and are often reported as "X" or I/L. Similarly, some specific combinations of small amino acid residues could have the same mass as a bigger amino acid residue.

In the case of I/L residues, the ability to distinguish between these two isobaric amino acids in a sequence can be crucial in several instances. Since protein sequences can be determined by mass spectrometry, each uncertainty for determining the nature of the right isobaric amino acid in the sequence increases by "2 k" the number of possibilities where "k" is the number of one of the two isobaric amino acids in a protein sequence. If the goal of sequencing a protein is to extract information in order to generate recombinant protein, these numbers of possibilities directly translate into the number of genes, and thus the gene primers to be generated. Thus, the ability to assign the correct isobaric amino acid reduces the number of primers to be used. This translates into a significant cost and time reduction.

Several MS-based methods have been developed to distinguish between Isoleucine (I) and Leucine (L) in a peptide sequence. Earlier methods relied on using higher collision energy where specific unique fragments to each of the isobaric amino acids can be identified (Falick et al 1993). However, those types of MS instruments are rarely used or available in laboratories performing peptide sequencing. Other methods include different MS ionization strategies (Nakamura et al 1990; Waern et al 1978) or derivatisation for detection in negative mode (Ramsay et al 1995; Lindh et al 2000), neither of which are practical in a modern proteomics laboratory.

Most of the MS instruments used in proteomics operate with lower collision energy for peptide fragmentations, thus cannot be easily used to distinguish between the two isobaric residues. Recent efforts have been made by Armirotti and co-workers using lower energy types of instruments (Armirotti et al., 2007). Their method is based on the detection of a specific low mass ion signature (Immonium ions). This approach allows for the presence of one of the isobaric amino acids to be reported, however, this method cannot be used to easily pinpoint the position of the right amino acid in a sequence, especially in the case where both isobaric amino acids are present in the same sequence.

Recently, Lebedev and co-workers have published papers addressing the challenge posed by identifying the proper isobaric amino acid in a peptide sequence (Zhokhov et al. 2017; Lebedev et al 2014). They mostly rely on detecting specific ion fragments, w ions, which allow for distinguishing Isoleucine from Leucine. They rely on the use of Electron Transfer Dissociation (ETD), which generates c and z ions. The latter could further fragment under certain conditions to generate w ions which have a different m/z signature for Leucine and Isoleucine. While this method is acceptable for the use of trypsin as a protease, and can work to distinguish Isoleucine from Leucine in a non-tryptic peptide in some cases, a large number of Isoleucines and Leucines will not be easily assigned for those non-tryptic peptides.

Although trypsin is the main protease of choice for most proteomics work, the complete sequencing of a protein often requires the use of different proteases having different protein cleavage rules in order to obtain overlapping peptide sequences or simply in order to increase the chance of detecting a portion of a sequence which otherwise is not easily detectable. One main drawback often observed when using other proteases is the poor quality of the ions resulting from C-terminal fragmentation. Trypsin is therefore the dominant protease in the proteomics market due to, among other things, the quality of the ions generated which is not found with other proteases.

Several peptide derivatisation strategies have been developed to modify peptide properties, including increasing their ionization efficiency (Mirzaei & Regnier, 2006) their charge state (Frey et al., 2013; Krusemark et al 2011, Perkins & Fischer 2010), or simply allowing their quantitation (e.g. commercially available methods such as iCAT, iTRAQ and TMT). Most of the common approaches target primary amine groups (i.e. the peptide N-terminal or Lysine side-chains) or thiol group (cysteine side-chains). However, due to its lower reactivity, C-terminal derivatisation of peptides has been explored to a much lesser extent.

Among the few approaches that have been developed for C-terminal derivatisation, the most common method has been esterification of the carboxylic function. However, a neutralization of the charge state results from such a modification (Goodlett et al., 2001). Frey et al. (2013) have developed an approach based on C-terminal amidation with primary amine using (7-Azabenzotriazol-1-yloxy)tripyrrolidinophosphonium hexafluorophosphate (PyAOP) as the coupling reagent, in order to increase both the charge state and fragmentation under Electron transfer dissociation (ETD) of tryptic peptides. Another approach is based on using N-(3-dimethylaminopropyl)-N'-ethylcarbodiimide hydrochloride (EDC) and 1-hydroxy-7-azabenzotriazole (HOAt) to couple 2-aminoethyl trimethylammonium (AETMA) (Ko & Brodbelt, 2012). However, the coupling reagent HOAt exhibits some explosive properties under certain conditions, thus requiring delicate handling.

Chemical coupling strategies to the C-terminal end of a peptide has been the subject of only few reviews (Al-Warhi et al, 2012, for example) and very few of these have been used in a proteomic context. Enzymatic trans-peptidation has been studied using different enzymes with a stronger emphasis on using carboxypeptidase Y (CPY). However, CPY shows a strong sequence-specific bias in terms of transpeptidation and most studies have been performed using simple peptide mixture (Breddam et al, 1980) or protein (Xu et al 2011).

As such, very few strategies are available to decipher between the two isobaric amino acids, Leucine and Isoleucine. The inventors have therefore sought to develop an approach for differentiating between isobaric amino acids when sequencing a peptide.

SUMMARY OF THE INVENTION

It is an object of the invention to provide an improved method for distinguishing isobaric amino acids during polypeptide sequencing.

The invention relates to the addition of a basic group at the C-terminal side of peptides to be analyzed by mass spectrometry, especially when using enzymes or cleavage strategies other than trypsin, Arg-C and lys-C. This allows the detection of peptide fragments which normally are not detectable by the mass spectrometer. These fragment ions include w ions, which can then be used to resolve possible conflict in the sequencing interpretation resulting from isobaric amino acids such as I/L, or amino acid combinations such as GG and GA for N and Q respectively.

Accordingly, there is provided herein a method for distinguishing isobaric amino acids and amino acid combinations of asparagine and glycine-glycine; glutamine and glycine-alanine; and/or glutamine and alanine-glycine, during polypeptide sequencing comprising the following steps:

obtaining a peptide of interest and/or digesting a polypeptide of interest with a protease or a chemical cleavage method to produce shorter peptides;

reacting the obtained and/or generated peptides with a coupling reagent capable of derivatizing the free C-terminal carboxylic acid function of the peptides, under conditions to add a basic functional group (a positive charge);

selecting a charge state of 2+ or more, and fragmenting the derivatized peptides in a mass spectrometer under conditions effective to generate at least w ions; and detecting said w ions by mass spectrometry, and identifying derivatized peptides which incorporate the additional mass of said basic functional group;

wherein positive charges are added to the free C-terminal carboxylic acid function of the peptide and/or polypeptide, and said w ions are analyzed to distinguish between the isobaric amino acids and amino acid combinations of: isoleucine and leucine; asparagine and glycine-glycine; glutamine and glycine-alanine; and/or glutamine and alanine-glycine.

In certain embodiments of the described method, the reacting step may involve chemical or enzymatic coupling of the basic functional group to at least the polypeptide's C-terminal end.

In further embodiments the coupling reagent may be a carbodiimide, for example, 1-ethyl-3-(3-dimethylaminopropyl) carbodiimide (EDC), Dicyclohexylcarbodiimide (DCC), or N,N'-Diisopropylcarpylcarbodiimide (DIC), or phosphonium ions such as (benzotriazol-1-yloxy)tris(dimethylamino)phosphonium hexafluorophosphate (BOP), (benzotriazol-1-yloxy)tris(pyrrolidino)phosphonium hexafluorophosphate (PyBOP), (7-Azabenzotriazol-lyloxy) tripyrrolidinophosphonium hexafluorophosphate (PyAOP), or aminium ions such as N-[(1H-benzotriazol-1-yl)(dimethylamino)methylene]-N-methylmethanaminium hexafluorophosphate N-oxide (N-HBTU), N-[(dimethylamino)-1H-1,2,3-triazolo[4,5-b]pyridin-1-ylmethylene]-N-methylmethanaminium hexafluorophosphate N-oxide (N-HATU), or 1-(1-pyrrolidinyl-1H-1,2,3-triazolo[4,5-b]pyridin-1-yl-methylene)pyrrolidinmium hexafluorophosphate N-oxide (HAPyU). Other coupling reagents will also be apparent to those of ordinary skill in the art.

In further embodiments, the basic functional group added to the polypeptide may be a cation such as a secondary, tertiary or quaternary amine or a guanidinium group. For instance, the basic functional group may be 3-dimethylamino-1-propylamine (3-DMP) or arginine methyl ester (MetArg), a dipeptide arginine-arginine with methyl ester at the C terminal (MetArg-Arg), 4-(trimethylamine) butylamine, 5-(dimethylamine)amylamine, 4-(2-aminoethyl)morpholine, N,N-diethyl-1,4-butanediamine, N,N-diisopropyl-1,5-pentanediamine, 4-(3-aminopropyl)morpholine, N,N-Dimethyldipropylenetriamine, 3-(Diethylamino) propylamine, 2-Amino-5-diethylaminopentane, or a phosphonium ion such as (3-aminopropyl)(triphenyl)phosphonium bromide, or a sulfonium ion such as (3-amino-3- carboxylpropyl)dimethyl sulfonium. Other basic functional groups will also be apparent to those of ordinary skill in the art.

In other embodiments, an additive may be used together with the coupling reagent in the reacting step to facilitate derivatization, such as ethyl cyano(hydroxyimino)acetate (OXYMA), (1-Cyano-2-ethoxy-2-oxoethylidenaminooxy) dimethylamino-morpholino-carbenium hexafluorophosphate (COMU), 2-Cyano-2-(hydroxyimino)acetic acid ethyl ester, potassium salt (K-OXYMA), or 1-[Bis(dimethylamino)methylene]-1H-1,2,3-triazolo[4,5-b]pyridinium 3-oxid hexafluorophosphate (HATU). Other additives will also be apparent to those of ordinary skill in the art.

In the described method a further step may be carried out in which lysine residues on the polypeptide are blocked, for example, by guanidisation using O-methylisourea under conditions effective to convert the lysine groups into a homoarginine group. The lysine sidechain can also be dimethylated or diethylated. In those cases, the charge state of lysine is kept. On the other hand, the lysine sidechain positive charge can be neutralized by acetylation or propionylation. Finally, the lysine residues can be left unmodified. By modifying or blocking lysines in this manner prior to derivatisation, it is possible to reduce side-reactions since the primary amine group of lysine is often the target of side reactions with some of the coupling or additive reagent mentioned above. It also reduces the probability of forming covalent peptide to peptide bonds (peptide to peptide instead of functional group to peptide), although the functional group is often added in significant molar excess compared to the peptide to reduce the probability of peptide to peptide coupling.

In other embodiments of the method, a further step of blocking the free amino group at the N-terminus of the polypeptide may be included. As an example, the N-terminus of the polypeptide may be blocked with di-tert-butyl dicarbonate, or simply dimethylated, diethylated, acetylated or propionylated as lysine residues. If included, this step will typically be performed at the same time as lysine modification.

Cleaning steps can also be incorporated into the method, whereby the derivatized peptides are cleaned e.g. using a chromatography column or liquid phase separation. For instance, the derivatized peptides may be cleaned by solid-phase extraction (SPE), using reverse phase, normal phase or ion exchange SPE or HPLC. Alternatively, or in addition, the polypeptide of interest and/or the derivatized peptides may be cleaned by liquid phase separation, e.g. using water saturated ethyl acetate, and dried, e.g. using a concentrator under low pressure, or using other organic solvents such as chloroform, dichloromethane or ether.

In embodiments of the described method, the lysine (K) residues could be either left intact or (if blocked) may, for example, have an additional mass of 42.021798 Da (1C 2N 2H) due to guanidisation or the N-terminal and lysine been dimethylated (+28.0313 Da 2C 4H), Acetylated (+42.0106 Da 2C 2H 1O) or propionylated (+56.0262 Da 3C 4H 1O).

In further embodiments of the described method, the aspartic (D) and glutamic acid (E) residues acid as well as the C-terminal carboxylic acid function of the polypeptide will have an additional mass, e.g. of 170.116761 Da (4N 7C 14H 1O) due to MetArg coupling, or 84.1051 Da (2N 5C 14H-(2H 1O)) using 3-DMP or 112.136433 Da (2N 7C 18H-(2H 1O)) using 5-(dimethylamino)amylamine or 326.2179 Da (13C 26H 8N 2O) using Arg-Arg-omet.

BRIEF DESCRIPTION OF THE DRAWINGS

These and other features of the invention will become more apparent from the following description in which reference is made to the appended drawings, wherein.

DETAILED DESCRIPTION

The inventors have developed a method of polypeptide sequencing which improves the generation of C-terminal fragment ions and additionally enables discrimination between isobaric amino acids. The method includes a step of peptide labelling to increase the C-terminal charge state and C-terminal fragment ionisations, specifically such that w-ions are obtained and used to distinguish between possible isobaric amino acids or other difficult to resolve amino acid combinations.

Figure 2:
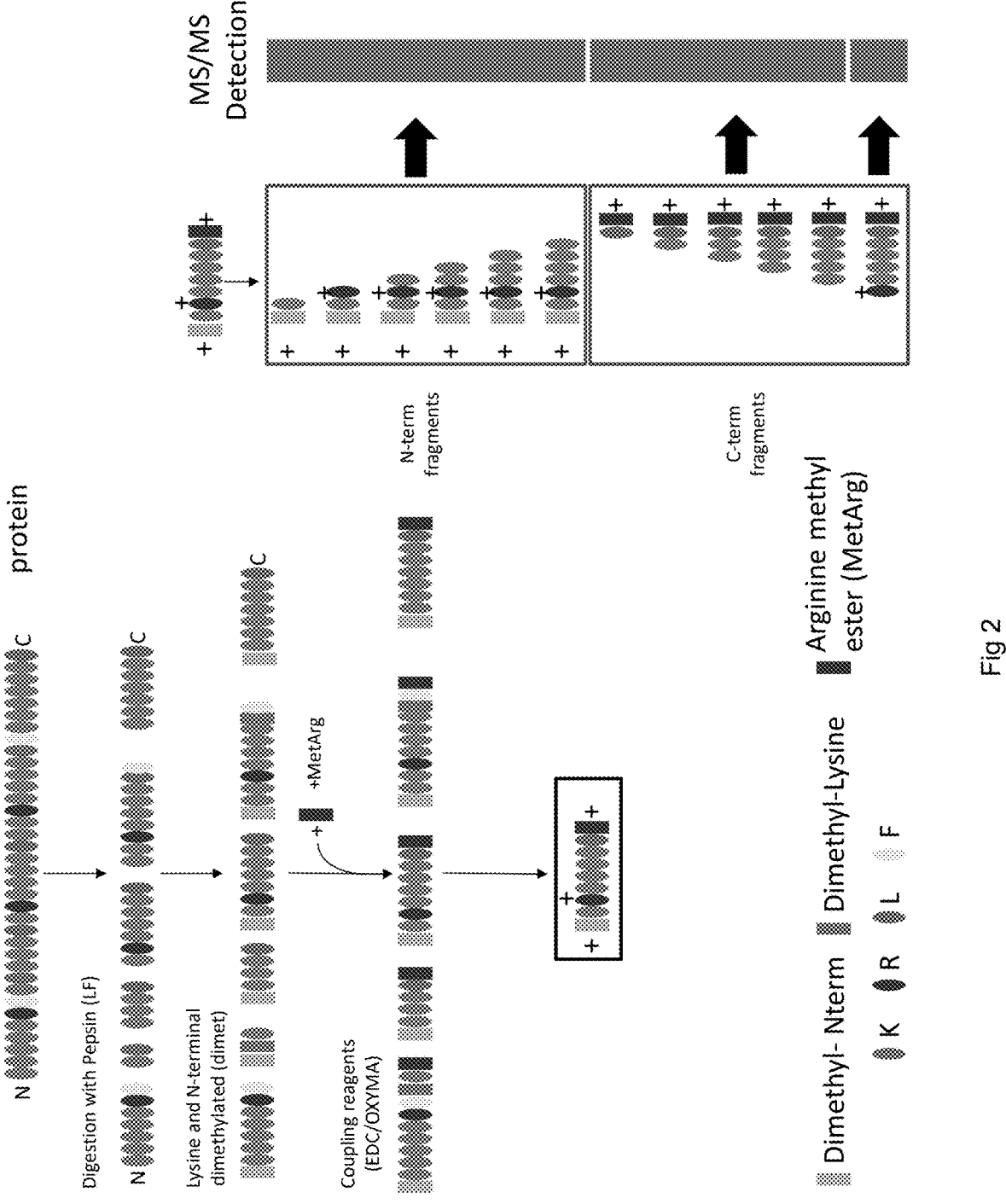
FIG. 2 illustrates an embodiment of the method described herein, involving an Arginine methyl ester (MetArg) labelling process applied to the same protein shown in FIG. 1 (left), when using pepsin as the protease for digestion. The "detectability" of the theoretical generated ions (from either N-terminal or C-terminal peptide extremities) is shown on the right either with green for detectable peptide or red if not detectable due to the lack of ionization.

The combination of C-terminal labelling as described, together with pepsin enzyme digestion, is especially advantageous as it allows for the z1 fragment (w1) to be obtained. Pepsin often cleaves at the C-terminal side of Leucine preferentially, which allows for an easier confirmation for that particular amino acid. A schematic overview of how the described method improves fragment detectability is shown in FIG. 2.

In particular, the method involves distinguishing isobaric amino acids and amino acid combinations of asparagine and glycine-glycine; glutamine and glycine-alanine; and/or glutamine and alanine-glycine, during polypeptide sequencing as follows:

a peptide of interest is obtained and/or a polypeptide of interest is digested with any protease, such as but not limited to pepsin, Asp-N, chymotrypsin, lys-C, elastase, Glu-C, thermolysin or trypsin, or generated using chemical cleavage such as but not limited to cyanogen bromide (CNBr), 2-(2-nitrophenylthio)-3H-indole (BNPS-skatole), formic acid, 2-nitro-5-thio-cyano-benzoic acid (NTCB), 1-cyano-4-dimethylam-minopyridinium tetrafluoroborate (CDAP), to produce shorter peptides from proteins;

the peptides are then reacted with a coupling reagent capable of derivatizing the free C-terminal carboxylic acid function of the polypeptide (which include the C-terminal end of peptides and sidechain of aspartic and glutamic acids), under conditions effective to add a basic functional group;

a charge state of 2+ or more is selected, and the derivatized peptides are fragmented in a mass spectrometer under conditions effective to generate at least w ions; preferably y,z and w ions and the w ions, preferably y, z and w ions, are then detected using mass spectrometry, and derivatized peptides which incorporate the additional mass of said basic functional group are identified.

Positive charges are added to the free C-terminal carboxylic acid function of the polypeptide, and the w ions are analyzed to distinguish between the isobaric amino acids and amino acid combinations. In particular, the method allows for discrimination between: isoleucine and leucine; asparagine and glycine-glycine; glutamine and glycine-alanine; and/or glutamine and alanine-glycine.

As isoleucine and leucine have the exact same masses (same chemical composition as well), common fragment ions reflecting their presence in a peptide sequence such as b,c,y,z ions are identical, thus those ions will not allow distinguishing between those 2 amino acids. However, z and a ions, due to their unstable nature, generate secondary ions (w and d respectively), where for example a leucine at the N-terminal of a z ion can lose a propyl group (−43.0548 amu 3C 7H) and an isoleucine can lose either an ethyl group (−29.0391 amu 2C 5H) or to a lesser extent a methyl group (−15.0235 amu CH3). In consequence, w ions resulting from Leucine or Isoleucine have different masses thus allowing proper distinction between those two amino acids. In a similar way, the 2 residues glycine-glycine (GG with an isotopic mass of 114.0429 amu) have the same masses of the single residue asparagine (N with an isotopic mass of 114.0429 amu). The 2 residues GG at the N-terminal end of a z ion, due to their small side chains, do not generate w ions, on the other end, asparagine (N) at the N-terminal end of a z ion will lose 44.0136 amu to generate a w ion (loss of 1C 1O 1N 2H). In a similar way, Glutamine residue (Q with an isotopic mass of 128.0586 amu) has the same mass as the combination of the two residues glycine alanine (isotopic mass of 128.0586 amu). The sidechain of the 2 residues glycine and alanine are too small to generate any w ions, however a Glutamine at the N-terminal of a z-ion will lose 58.0293 amu to generate a w ion (loss of s 2C 1N 1O 4H). In the described examples, the larger residues (either, I, L, N or Q), if located at the N-terminal end of a z-ion will lose most of their side chain leaving a shorter sequence, often a double bond CH2 in the case of Leucine, asparagine and glutamine. Those lost are only possible if the residue has initially at least 2 carbons in their sidechains, which is not the case for Glycine and Alanine. Finally, in order to have w-ion, it is required to have z-ion and in order to have z-ion there must be a positive charge at the C-terminal end. This is done using derivatisation, for example with MetArg.

Figure 10:
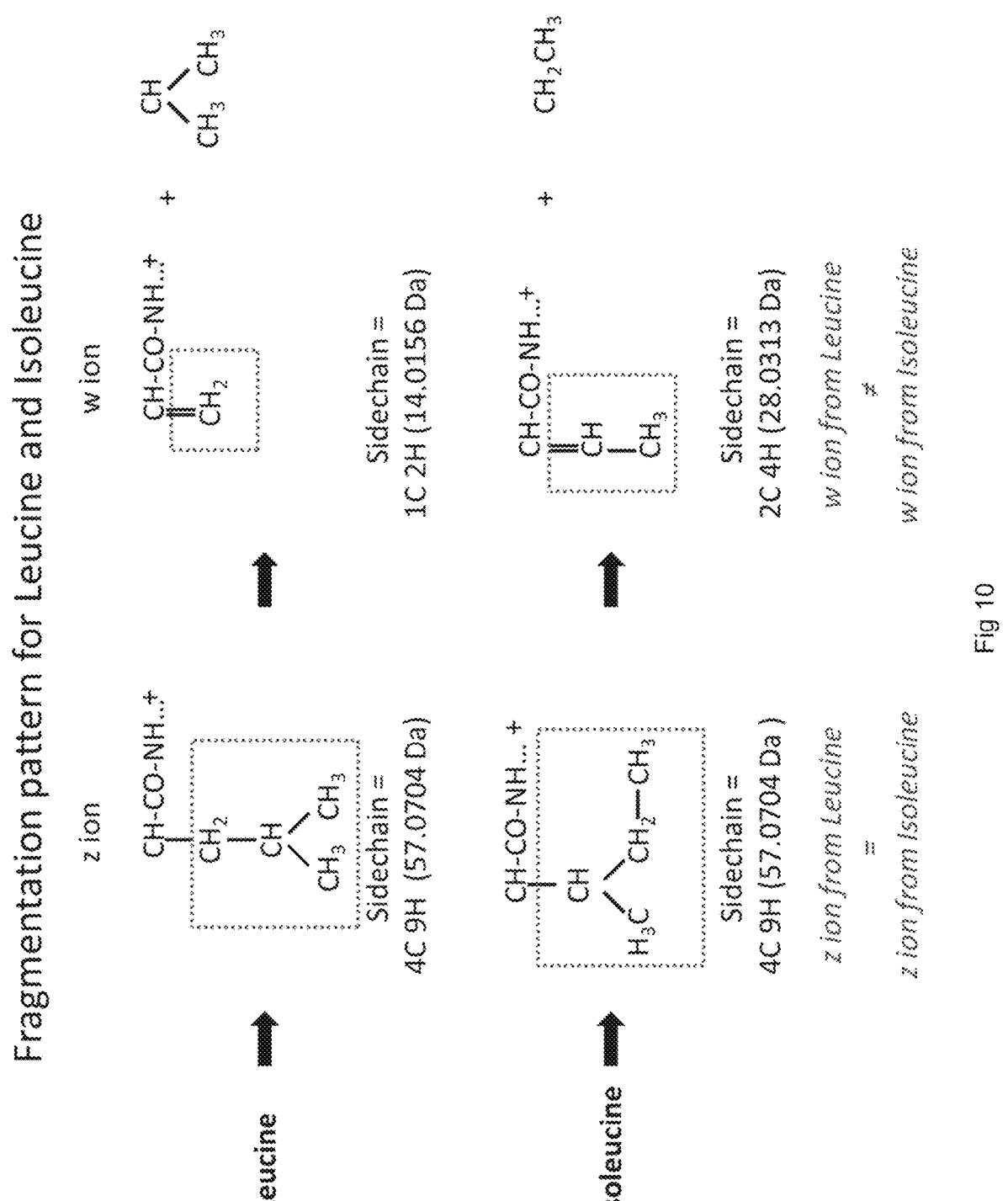
FIG. 10 illustrates the chemical nature of the z and w ions generated in the case of Leucine and Isoleucine at the N-terminal end of a z ion. Although both residues have the same composition, they can be differentiated by their w ions.
Figure 11:
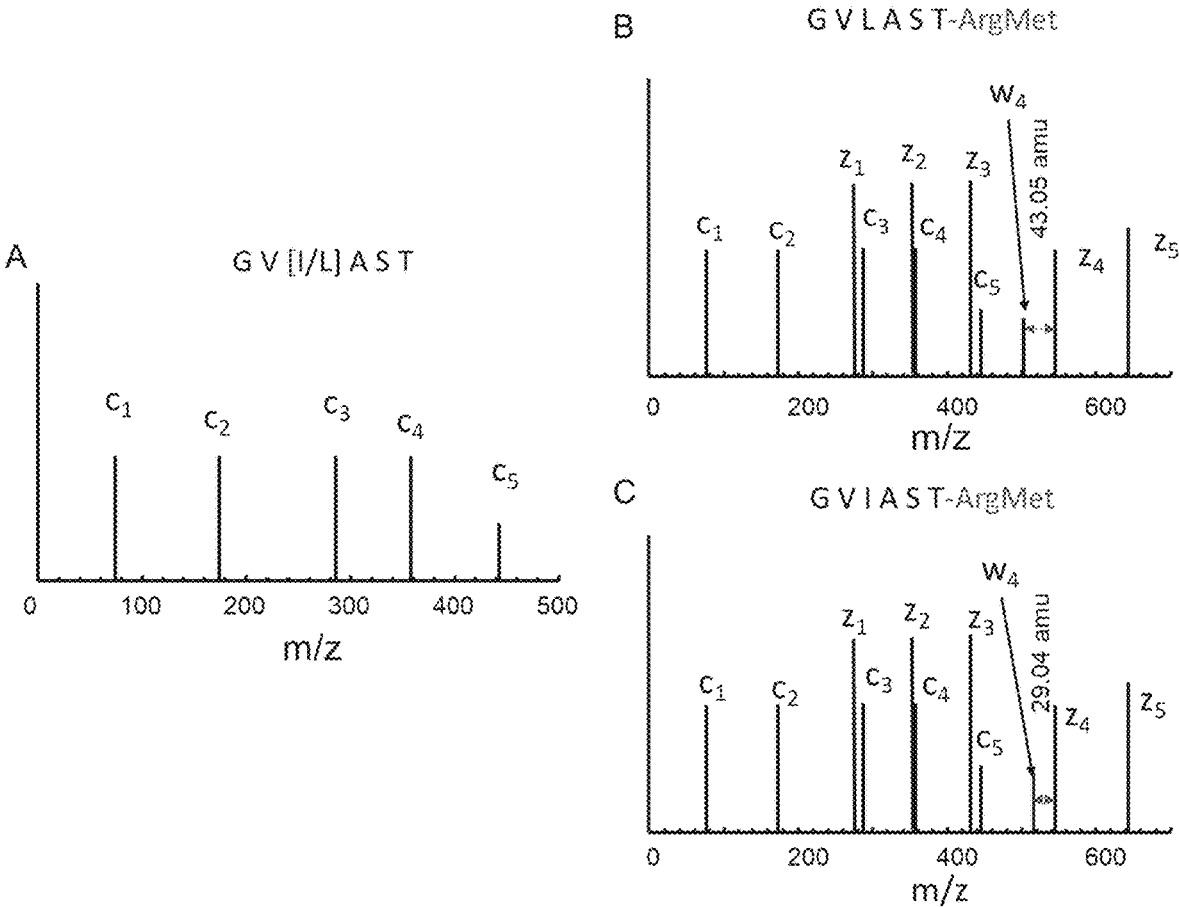
FIG. 11: (A) illustrates the hypothetical peptide sequence GV(I/L)AST, SEQ ID NOS: 8 and 9, analyzed in EThcD (simulated spectra, not a real experiment). In 11A, the peptide is not labelled, the ionisable fragments are exclusively from the N-terminal end (simulated c ions). No z or w ions are easily generated for that type of sequence as no ionisable group are present. In 11B the sequence is GVLASTX where X is Arginine methyl ester (SEQ ID NO: 16); the Arginine methyl ester (MetArg) adds an additional mass of 170.116671 amu. Both N-terminal and C-terminal fragments (c and z ions respectively are detectable in that case). An additional ion is highlighted (w ion) as a loss of 43.05 amu, confirming the presence of a leucine at the N-terminal end of z4. In 11C the sequence is GVIASTX where X is Arginine methyl ester (SEQ ID: 17); the leucine is replaced by an isoleucine at the N-terminal end of the z4 ion fragment. The resulting w ion shows instead a loss of 29.04 amu. Both B and C spectra are similar except for the w ions fragments which are different due to the I/L at the N-terminal side of the hypothetical z4 ions.

An example of a w ion resulting from Leucine and Isoleucine is illustrated in FIG. 10. FIG. 11, a figure of principle illustrates MS/MS spectra of a short peptide without labelling (FIG. 11A) and the same peptide with C-terminal labelling with a Leucine in the $3^{rd}$ position from the peptide N-terminal end (FIG. 11B) or C-terminal labelled with in this case an Isoleucine in the $3^{rd}$ position from the peptide N-terminal end. The 2 spectra in FIGS. 11B and C are very similar, with only a small shown difference associated to the presence of a Leucine or an Isoleucine in the sequence. This is discussed in more detail in the experiments discussed below.

In specific embodiments of the method, the derivatization of the peptide as described facilitates the correct assignment of isoleucine vs. leucine in the peptide sequence, especially in cases where a protease other than trypsin is used for digestion. Embodiments of the described method also enable the resolution of other ambiguities resulting from amino acid residues and combinations having the same mass.

Accordingly, the described method facilitates:

(i) C-terminal sequencing by mass spectrometry of peptides having no basic residues on the C-term extremity and (ii) the distinction between isobaric amino acids, such as isoleucine and leucine, or isobaric amino acid combinations such as asparagine (N) which has the same mass as 2 glycines (GG), and glutamine (Q) which has the same mass as an alanine and glycine (AG or GA). This distinction is possible due to the generation of w ions, resulting from adding a positive functional group at the C-terminal end of the peptide.

As described in further detail below, all of these isobaric combinations can be deciphered through the detection of w-ions, for example using EThcD (Electron-Transfer/Higher-Energy Collision Dissociation), Hot Electron Capture Dissociation (HECD), ETD-HCD-MS3, Activated Ion Electron Transfer-Dissociation (AI-ETD), or AI-ETD combined with post-activation using infrared multiphoton activation, (AI-ETD+) or ETD supplemented with UV-photo-dissociation (ETUVPD) or simply UV-photo-dissociation (UVPD).

Figure 1:
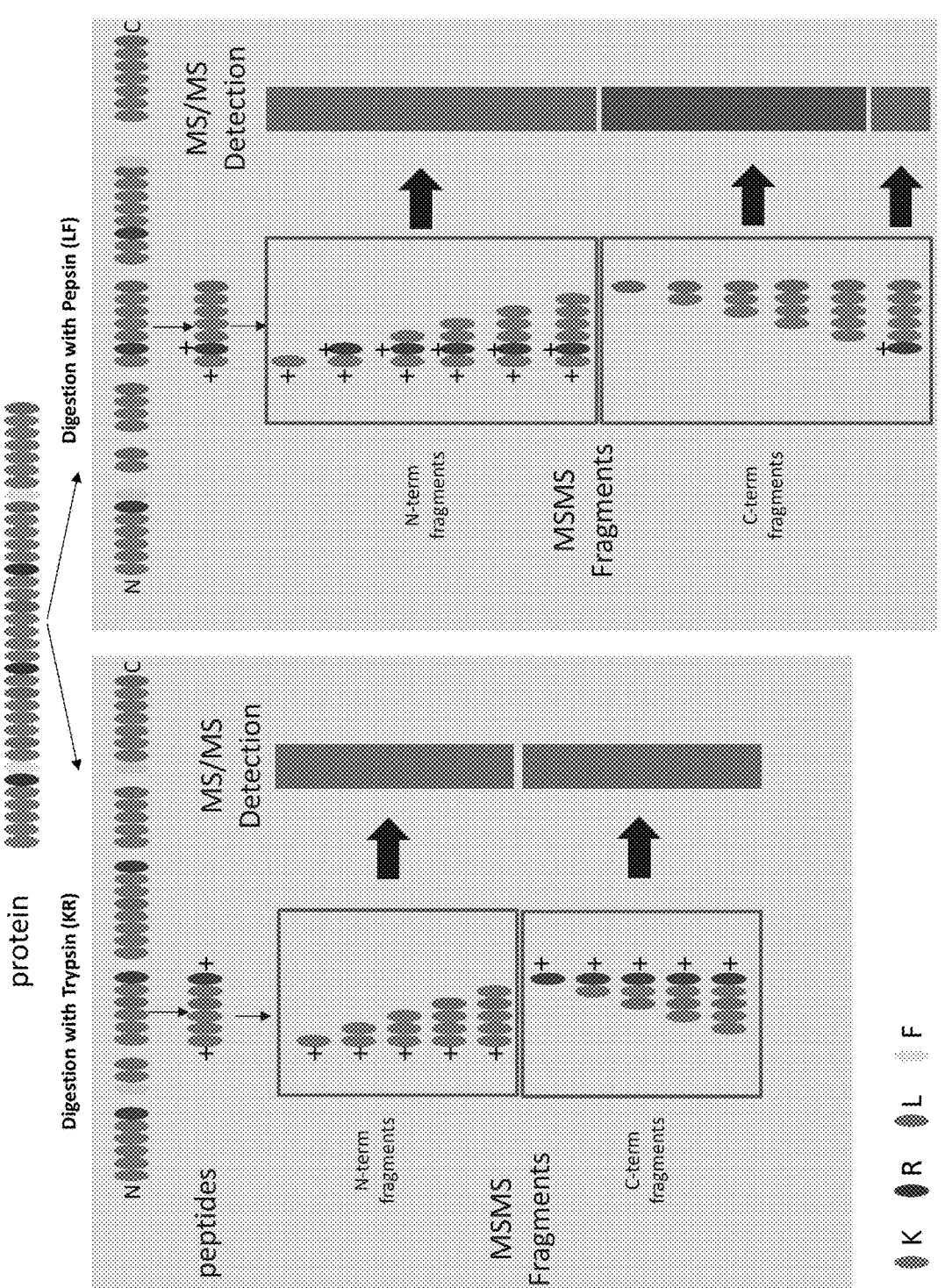
FIG. 1 illustrates a comparison of the peptides generated using 2 different proteases, trypsin (left) and pepsin (right), and the MS/MS detectability of selected peptide fragment ions for both proteases. Some of the C-terminal fragments are not detectable in the case of a pepsin digestion as no ions are generated, more specifically, if those fragments do not contain a basic residue such as K, R or H (illustrated by the red bar on the right side of the Figure).

The described method involves the analysis of ions resulting from peptide C-terminal fragmentation. These ions can be generated using a specific protease-trypsin-which cuts proteins into shorter peptides by cleaving at the C-terminal side of arginine and lysine. Arginine and lysine are basic residues, carrying a positive charge under acidic conditions, which is an essential property for positive ion detection by mass spectrometry. C-terminal ions are relatively rarely produced by other proteases, thus, distinguishing isoleucine from leucine using proteases other than trypsin is more tedious and relies on the presence of a basic residue close to the cleavage site, which is not always the case for the majority of proteins. An illustration of the impact of using trypsin or pepsin on the ions and fragments that can be detected is shown in FIG. 1. The proposed derivatization allows generation of C-terminal ions with any proteases, such as but not limited to Asp-N, Glu-C, chymotrypsin, elastase, trypsin-N, lys-N and pepsin.

The use of a mass spectrometric method as described herein, which is based on generating w-ions, in combination with a labelling or peptide derivatization step, allows for the addition of a positive charge onto any peptides at its C-terminal end independently of the used proteases or chemical cleavage. This allows the method to discriminate isoleucine from leucine and other isobaric amino acid combinations, which is particularly challenging during polypeptide sequencing.

Definitions

The term "functional group" refers to any molecule that can be coupled to the carboxyl group at the C-terminal end of a peptide, and which bears a free basic group. This may include, without limitation, a cation such as a secondary, tertiary or quaternary amine, or a guanidine group (e.g. 3-Dimethylamino-1-propylamine (3-DMP) or Arginine methyl ester (MetArg)), 4-(trimethylamine) butylamine, 5-(dimethylamine)amylamine, 4-(2-aminoethyl)morpholine, N,N-diethyl-1,4-butanediamine, N,N-diisopropyl-1,5-pentanediamine, 4-(3-aminopropyl)morpholine, N,N-Dimethyldipropylenetriamine, 3-(Diethylamino)propylamine, 2-Amino-5-diethylaminopentane, a phosphonium ion such as (3-aminopropyl)(triphenyl)phosphonium bromide, or a sulfonium ion such as (3-amino-3-carboxylpropyl)dimethyl sulfonium.

The term "coupling reagent" refers to a reagent that is capable of derivatizing the free C-terminal carboxylic acid function of the peptide of interest, and optionally also the carboxylic acid function of any glutamic and aspartic acid residues in the peptide sequence, thereby adding the aforesaid functional group. Examples of coupling reagents include but are not limited to carbodiimides (e.g. 1-Ethyl-3-(3-dimethylaminopropyl) carbodiimide (EDC)), Dicyclohexylcarbodiimide (DCC), or N,N'-Diisopropylcarpylcarbodiimide (DIC), or phosphonium ions such as but not limited to (benzotriazol-1-yloxy)tris(dimethylamino)phosphonium hexafluorophosphate (BOP), (benzotriazol-1-yloxy)tris(pyrrolidino)phosphonium hexafluorophosphate (PyBOP) (7-Azabenzotriazol-1yloxy)tripyrrolidinophosphonium hexafluorophosphate (PyAOP), or aminium ions such as N-[(1H-benzotriazol-1-yl)(dimethylamino)methylene]-N-methylmethanaminium hexafluorophosphate N-oxide (N-HBTU), N-[(dimethylamino)-1H-1,2,3-triazolo[4,5-b]pyridin-1-ylmethylene]-N-methylmethanaminium hexafluorophosphate N-oxide (N-HATU), 1-(1-pyrrolidinyl-1H-1,2,3-triazolo[4,5-b]pyridin-1-yl-methylene)pyrrolidinmium hexafluorophosphate N-oxide (HAPyU).

The term "additive" refers to a reagent that is commonly used together with a coupling reagent in a derivatization reaction, in order to enhance reactivity. Examples of additives include but are not limited to Ethyl cyano(hydroxyimino)acetate (OXYMA), (1-Cyano-2-ethoxy-2-oxoethylidenaminooxy)dimethylamino-morpholino-carbenium hexafluorophosphate (COMU), 2-Cyano-2-(hydroxyimino) acetic acid ethyl ester, potassium salt (K-OXYMA), and 1-[Bis(dimethylamino)methylene]-1H-1,2,3-triazolo[4,5-b] pyridinium 3-oxid hexafluorophosphate (HATU).

EXAMPLES

(I) Functional Group Analysis

As discussed above the types of functional group that can be used in the described method can be varied, as long as they can be coupled to a free carboxylic acid group of a peptide and have a free basic group. Three different functional groups (molecules) were tested: 3-Dimethylamino-1-propylamine (3-DMP), arginine methyl ester (MetArg), and the dipeptide arginine-arginine-methyl ester (RR-omet).

The coupling between the functional group and the peptides of interest in this example was carried out using the coupling reagent 1-ethyl-3-(3-dimethylaminopropyl) carbodiimide (EDC), with ethyl cyano(hydroxyimino)acetate (OXYMA) as an additive/enhancer.

Using these reagents, any free carboxylic acid function will be derivatised, and thus the peptide C-terminal amino acid as well as any glutamic and aspartic acids in the peptide sequence will be coupled with (a) arginine methyl ester if using MetArg—increasing the mass by 170.116761 Da (4N 7C 14H 1O), or (b) 3-Dimethylamino-1-propylamine if using 3-DMP increasing the mass by 84.105133 Da (2N 5C 12H-1O), or (c) arginine-arginine-methyl ester using RR-oMet increasing the mass by 326.2179 Da (13C 26H 8N 2O). A positive charge increase of 1 unit per functional group coupled will be added to the labelled peptide in the case of 3-DMP and MetArg and an increase to 2 units per functional group coupled will be added to the labelled peptide in the case of RR-oMet.

(II) Labelling Procedure: Example 1

The overall procedure presented below is applied to 10 ug of a peptide(s) resulting from a pepsin digest, however it can be applied to either smaller or larger amounts of a peptide mix and be scaled accordingly. It can also be applied to any other peptide mix that results from the use of any other protease or chemical cleavage.

1. Block Lysine with a guanidisation group (optional): In the presented case, the inventors used EDC/OXYMA, which can generate several side reactions. One of the most abundant side reactions is Lysine guanidisation (Lysine modified to Homoarginine). This particular modification does not affect the lysine ionization state, however, this side-reaction is often partial thus adding an additional level of unnecessary complexity. Thus, an optional step is envisioned in the described method to block all Lysine residues with a guanidine group using O-methylisourea at pH 10.5, thus all Lysines are then replaced by a homoarginine. To 10 ug of peptide digest, add 50 uL of a solution of 0.1 g/ml of O-methylisourea at 65° C. for 1 h. The reaction is then stopped by cleaning the peptide mixture on a reverse phase solid phase extraction device (RP-SPE) in order to remove extra coupling reagent which could interfere with the subsequent labelling steps.
2. Block free N-terminal with Di-tert-butyl dicarbonate, BOC (optional): To 10 ug of dry and clean digested peptide, add 8 uL BOC and 25 uL water; sonicate and incubate 1 h at room temperature (RT). This step is not necessary if the coupling reagent and the functional group are added both in excess and added at the same time.

Figure 3:
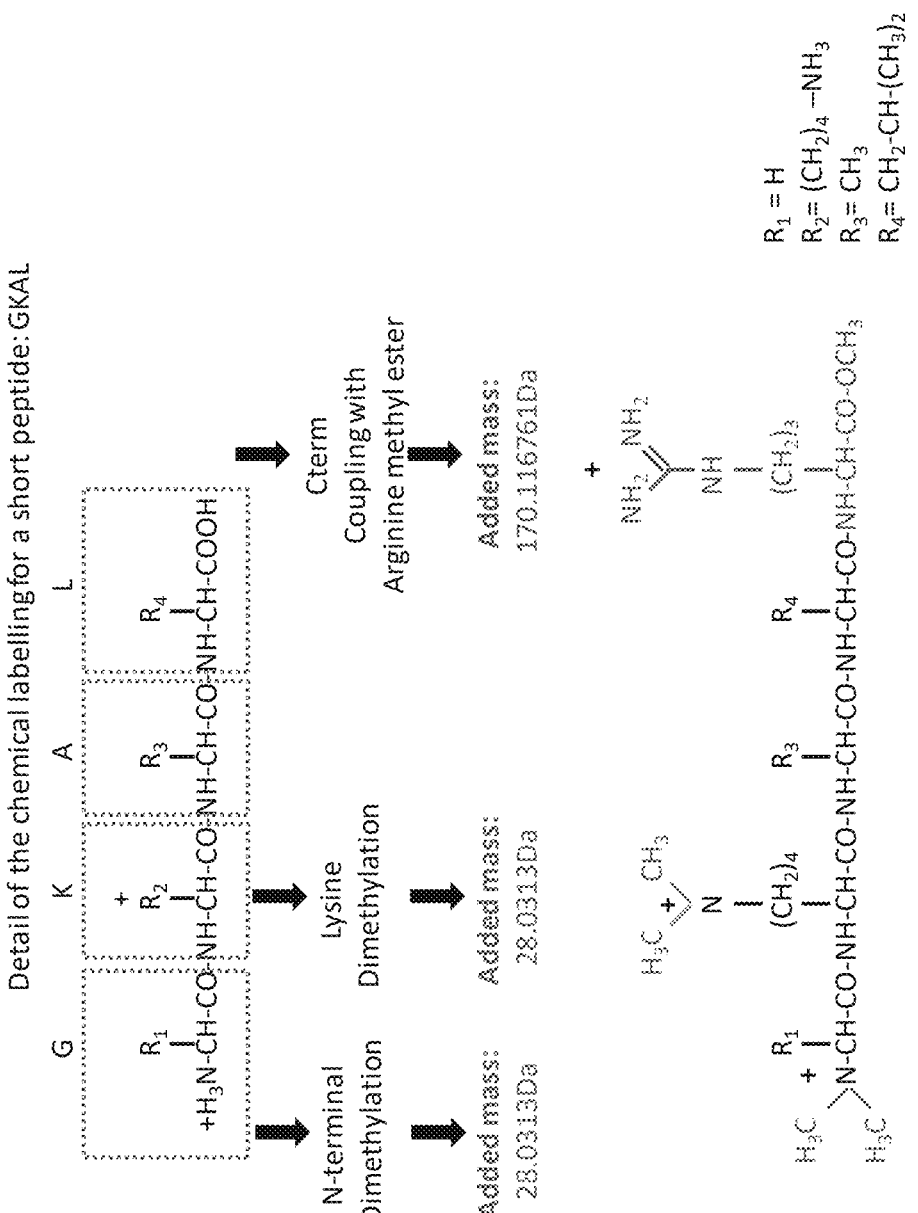
FIG. 3 illustrates an embodiment of the method described herein, involving an example of the MetArg labelling process for a short hypothetical peptide "GKAL". The blue chemical structure shows the dimethylation derivatisation of Lysine and the peptide N-terminal end (an optional step which reduces potential side reactions). The chemical structure in red shows the Arginine methyl ester group (MetArg) added to the peptide C-terminus. A MetArg group will also be added to most of the Aspartic and Glutamic acid side chains.

3. Clean-up: Peptides are either cleaned on SPE (reverse phase, normal phase or ion exchange) or by using liquid phase separation. In this case, water saturated ethyl acetate was used. Briefly, add to the sample 100 uL with MQW water, add 1 mL water saturated ethyl acetate, mix well, remove the upper layer and repeat the cleaning procedure with ethyl acetate 2-3 times to remove extra BOC reagent. The peptides are then dried using a concentrator under low pressure.
4. Peptide coupling: Peptides are reconstituted in 100 uL MQW $H_2O$, add 80 uL of Arginine methyl ester (32.5 mg/ml in a mix of $H_2O$ dimethylformamide, DMF 1:1). The pH is adjusted to 5-6 using 1N sodium hydroxide, 40 uL EDC (100 mg/ml in DMF:water 950:50) is added with 26 uL OXYMA (100 mg/ml in DMF), the pH is adjusted to 5-6 once again using 1N NaOH. The reaction is allowed to incubate overnight at RT. The reaction is then stopped by adding 50 uL of trifluoroacetic acid (TFA) and incubating for 1 h at RT.
5. Peptide clean-up: is performed using either SPE-RP or water saturated ethyl acetate as previously described in Step 3).
6. Peptide analysis by LC-MS: Most of the ions should have a charge state higher than 1, thus peptide selection for MS/MS can be performed by choosing a charge state of 2 and more even for non-tryptic peptides. Parameters for the search engine are as follows: Lysine, K can have an additional mass of 42.021798 amu (1C 2N 2H) due to guanidisation. The residues Aspartic (D) and Glutamic (E) acid as well as the peptide C-term can have an additional mass of 170.116761 Da (4N 7C 14H 1O), due to arginine methyl ester coupling. Positive charges are added to any added labelled Aspartic, Glutamic acid residues and the C-terminus. Additionally, in the case of any peptide labelling with arginine methyl ester, a reporter ion in the MS/MS spectra is found at 189.134626 amu (7C 4N 2O 16H 1H+) which allows for confirmation that the labelling method was successful. Illustrated in FIG. 2 is the overall labelling procedure, whereas FIG. 3 illustrates the chemical structure of the Lysine to Homoarginine conversion and an added MetArg at the C-terminus of a hypothetical peptide.

Labelling Procedure: Example 2

The overall procedure presented below is applied to 10 ug of a peptide(s) resulting from a pepsin digest.

1. Block Lysine and peptide N-terminal with a dimethyl group (optional): In the presented case, the inventors used EDC/OXYMA, which can generate several side reactions. Thus, another optional step is envisioned in the described method to block all Lysine residues and the peptide N-terminal with formaldehyde. The 10 ug peptide digest is reconstitute in 5 ul water:methanol (1:1), 1 ul formaldehyde 37% wt in water, 3 ul borane pyridine complex 8M and 3 ul of 4-methyl morpholine 1 h incubation followed by evaporation under low pressure; the dimethylation step can be repeated by labelling a second time in a similar way. The sample was then acidified with formic acid and reconstitute into 100 ul water and wash 3 times with ethyl acetate water saturated and then dried under low pressure. The Arginine methyl ester coupling was performed as describe in example 1.

2. Peptide coupling: Peptides are reconstituted in 100 uL MQW H₂O, add 80 uL of Arginine methyl ester (32.5 mg/ml in a mix of H₂O dimethylformamide, DMF 1:1). The pH is adjusted to 5-6 using 1N sodium hydroxide, 40 uL EDC (100 mg/ml in DMF:water 950:50) is added with 26 uL OXYMA (100 mg/ml in DMF), the pH is adjusted to 5-6 once again using 1N NaOH. The reaction is allowed to incubate overnight at RT. The reaction is then stopped by adding 50 uL of trifluoro-acetic acid (TFA) and incubating for 1 h at RT.

3. Peptide clean-up: is performed using either SPE-RP or water saturated ethyl acetate as previously described in example 1 Step 3).

4. Peptide analysis by LC-MS: Most of the ions should have a charge state higher than 1, thus peptide selection for MS/MS can be performed by choosing a charge state of 2 and more even for non-tryptic peptides. Parameters for the search engine are as follows: Lysine, K and peptide N terminal have an additional mass of 28.0313 amu (2C 4H) due to dimethylation. The residues Aspartic (D) and Glutamic (E) acid as well as the peptide C-term can have an additional mass of 170.116761 Da (4N 7C 14H 1O), due to arginine methyl ester coupling. Positive charges are added to any added labelled Aspartic, Glutamic acid residues and the C-terminus. Additionally, in the case of any peptide labelling with arginine methyl ester, a reporter ion in the MS/MS spectra is found at 189.134626 amu (7C 4N 2O 16H 1H+) which allows for confirmation that the labelling method was successful. Illustrated in FIG. 2 is the overall labelling procedure, whereas FIG. 3 illustrates the chemical structure of the Lysine to Homoarginine conversion and an added MetArg at the C-terminus of a hypothetical peptide.

Labelling Procedure: Example 3

C-Term Labelling Procedure Using PyAOP

The overall procedure presented below is applied to 10 ug of a peptide(s) resulting from a pepsin digest.

1. Block Lysine and peptide N-terminal: This was not done as the amine label reagent was added in molar excess compared to the amine from peptide, thus reducing significantly the chance to have peptide-peptide coupling.

2. C-term coupling reaction: An amine solution was made as follows: 100 mg of Methyl ester arginine (MetArg) was dissolved in 50 ul of water and 26 ul of 4-methyl morpholine (NMM). A coupling solution was made as follows: 66 mg of 7-Azabenzotriazol-1-yloxy)tripyrro-lidinophosphonium hexafluorophosphate (PyAOP) was dissolved in 145 ul of dimethylsulfoxide (DMSO). To the dry bug of peptide was added 10 ul of DMSO, then 14 ul of the amine solution and 6 ul of the coupling solution. The reaction was performed at room temperature overnight.

3. Reaction quenching and sample cleanup: 50 ul of TFA was added to the samples and 100 ul of water for 1 h. The sample was then cleaned to remove DMSO using 3 times 1 ml of water saturated ethyl acetate and one additional wash with 1 ml of chloroform. The sample was then dried using a centrifuge under low pressure (Speedvac), the dried labelled peptide digest was then reconstituted in 0.1% formic acid water buffer for LC-MS analysis.

4. Peptide analysis by LC-MS: Most of the ions should have a charge state higher than 1, thus peptide selection for MS/MS can be performed by choosing a charge state of 2 and more even for non-tryptic peptides. Parameters for the search engine are as follows: The residues Aspartic (D) and Glutamic (E) acid as well as the peptide C-term can have an additional mass of 170.116761 Da (4N 7C 14H 1O), due to arginine methyl ester coupling. Positive charges are added to any added labelled Aspartic, Glutamic acid residues and the C-terminus. Additionally, in the case of any peptide labelling with arginine methyl ester at the C-terminal end, a reporter ion in the MS/MS spectra is found at 189.134626 amu (7C 4N 2O 16H 1H+) which allows for confirmation that the labelling method was successful.

C-Term Labelling Procedure Using EDC-OXYMA on Solid Phase Extraction Reverse Phase Column (SPE): Example 4

The example is a chymotrypsin digest of Bovine Serum Albumin (BSA) 10 ug. A 25 mg Solid Phase Extraction (SPE) column Bond Elut C18 LMS lcc 25 mg beads volume (part no 12105021 from Agilent), was opened and the reverse phase packing media reconstituted in 1 ml acetoni-trile to generate a slurry. The RP C18 LMS frits was cut in small pieces and one small piece was introduced in a 200 ul pipette tip to act as a frit/filter to retain the media. 100 ul of the slurry was used and added on top of the frit in the 200 ul pipette tip. Another strategy consists of directly using without any modification an Evosep tip, although the bind-ing capacity is closer to 2 ug peptides instead of bug for the homemade Bond Elut SPE tip. A positive pressure was applied to the tip in order to force solvent to flow while the Reverse phase (RP) packing media were kept on top of the frit. Initially a 100 ul of Methanol was added to the tip and passed through by gravity flow. 50 ul of Acetonitrile was added and the column was conditioned with 80 ul of water. A 2-10 ug BSA peptide digest in 50 ul of water was added to the conditioned SPE tip. The peptide digest is retained on the SPE tip (either homemade Bond Elut or Evosep tip) and washed with 40 ul water. A dimethylation solution was made as follows: 21 ul of formaldehyde 37% and 7.5 mg of cyanoborohydrate were combined and the solution was completed to 1 ml water. 150 ul of the dimethylation solution was allowed to pass through the tip and the RP resin was immerged in the dimethylation solution overnight at room temperature.

The bound sample on the SPE tip was washed 2 times with 50 ul H₂O; Three coupling solutions were made. solution 1: 50 mg of EDC in 950 ul DMF+50 ul H₂O, solution 2: OXYMA 100 mg in 100 ul DMF, solution 3: 52 mg MetArg in 400 ul H₂O+400 ul DMF.

To the sample, 2 different methods for on-column C-termi-nal labelling were used:

Method 1: 200 ul of H₂O+26 ul solution 1+40 ul solution 2 and 80 ul solution 3+20 ul NaOH 1N; all mixed together and let flow through the column.

Method 2: is a 2-step processes where step 1 is the carbox-ylic acid activation with 200 ul of H₂O+26 ul solution 1+40 ul solution 2 and left on the column for 5-10 min; then step 2 is a coupling reaction which is done as follows: a 50 ul of a mix of (50 ul of solution 3+150 ul of H₂O+10 ul NaOH)

is added to the SPE tip and the RP media is immerged in this solution for 2 h. The activation and coupling step can be repeated another time.

The samples were then washed with 3×50 ul 0.1% Formic acid water; the RP tips were incubated in a Eppendorf tube for 1 h with 0.1% FA water (in order to hydrolyze the excess of the coupling reagent). The labelled peptide were then eluted with 100 ul acetonitrile and dried under low pressure (Speedvac), the dried labelled peptide digest was then reconstituted in 0.1% formic acid water buffer for LC-MS analysis. Regarding the Evosep tip, Elution was performed online on the Mass spectrometer using the suggested protocol proposed by the vendor.

Peptide analysis by LC-MS: Most of the ions should have a charge state higher than 1, thus peptide selection for MS/MS can be performed by choosing a charge state of 2 and more even for non-tryptic peptides. Parameters for the search engine are as follows: The residues Aspartic (D) and Glutamic (E) acid as well as the peptide C-term can have an additional mass of 170.116761 Da (4N 7C 14H 1O), due to arginine methyl ester coupling. Positive charges are added to any added labelled Aspartic, Glutamic acid residues and the C-terminus. Additionally, in the case of any peptide labelling with arginine methyl ester, a reporter ion in the MS/MS spectra is found at 189.134626 amu (7C 4N 2O 16H 1H+) which allows for confirmation that the labelling method was successful. Finally, Lysine, K and peptide N terminal have an additional mass of 28.0313 amu (2C 4H) due to dimethylation. On-column labelling strategy allows the overall C-terminal labeling process to be automatized and to reduce the usage of solvents such as ethyl acetate.

Labelling Procedure: Example 4: C-Term Labelling Procedure Using PyAOP and the Dipeptide Reagent Arginine-Arginine-Methyl Ester Reagent: Example 4

The overall procedure presented below is applied to 10 ug of a synthetic peptide Leucine Enkephalin (Sigma Aldrich L9133).

1. Block Lysine and peptide N-terminal: This was not done as the amine label reagent was added in molar excess compared to the amine from peptide, thus reducing significantly the chance to have peptide-peptide coupling.
2. C-term coupling reaction: An amine solution was made as follows: 100 mg of Methyl ester arginine-Arginine (Arg-Arg-omet) was dissolved in 50 ul of water and 26 ul of 4-methyl morpholine (NMM). A coupling solution was made as follows: 66 mg of 7-Azabenzotriazol-1-yloxy)tripyrrolidinophosphonium hexafluorophosphate (PyAOP) was dissolved in 132 ul of dimethylsulfoxide (DMSO). To the dry bug of peptide was added 10 ul of DMSO, then 14 ul of the amine solution and 6 ul of the coupling solution. The reaction was performed at room temperature overnight.
3. Reaction quenching and sample cleanup: 320 ul of 0.1% TFA was added to the samples, the sample was then cleaned to remove DMSO using 640 ul of chloroform 2 times. The sample was then dried using a centrifuge under low pressure (Speedvac), the dried labelled peptide digest was then reconstituted in 0.1% formic acid water buffer for LC-MS analysis.
4. Peptide analysis by LC-MS: Most of the ions should have a charge state higher than 1, thus peptide selection for MS/MS can be performed by choosing a charge state of 2 and more even for non-tryptic peptides.

Parameters for the search engine are as follows: The residues Aspartic (D) and Glutamic (E) acid as well as the peptide C-term can have an additional mass of 326.2179 Da (13C 26H 8N 2O), due to Arginine-Arginine methyl ester coupling. At least 2 positive charges are added to the C-terminus. Additionally, in the case of any peptide labelling with Arginine-arginine methyl ester at the C-terminal end, a reporter ion in the MS/MS spectra is found at 189.134626 amu (7C 4N 2O 16H 1H+) which allows for confirmation that the labelling method was successful.

(III) MS/MS Analysis of Non-Labelled and Labelled Peptide

Figure 4:
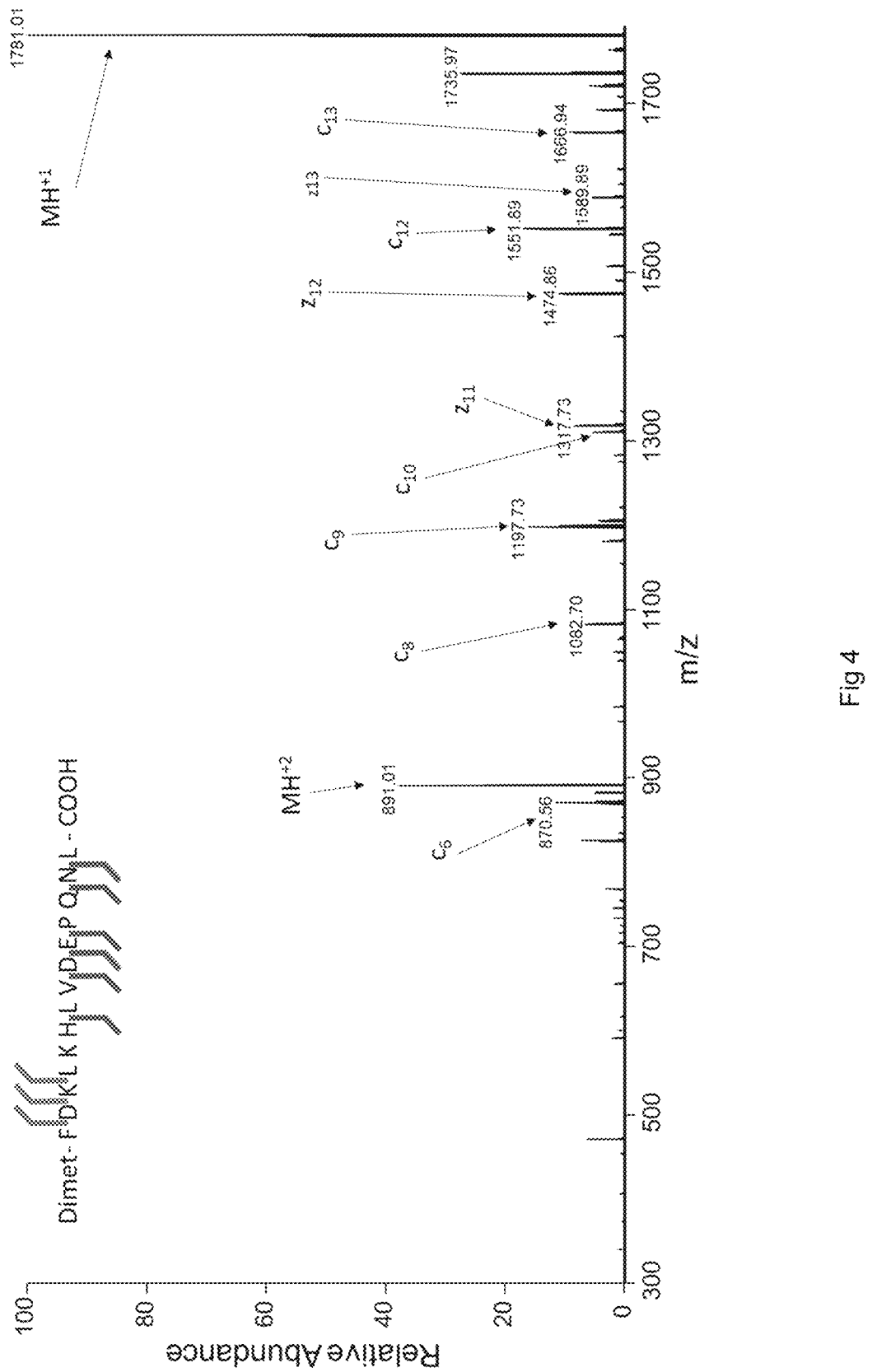
FIG. 4 illustrates EThcD MS/MS spectra of the peptide FDKLKHLVDEPQNL (SEQ ID NO: 1). The peptide has been only dimethylated at the N-terminal and lysine. The peptide is a 2+ at 890.51 amu (1.68 ppm). For the non C-terminal labelled form, there are no observed short C-terminal fragment ions in the MS/MS spectra (very few C-terminal fragment ions were generated, only $z_{11}$, $z_{12}$ and $z_{13}$ were detected, few c ions were as well detected from $c_6$ to $c_{13}$). Several forms of the same peptide were also found as 3+ and 4+ showing a similar pattern of fragmentation. On the upper left side of the Figure, ions resulting from the C-terminal side are shown in green (z-ions) while ions form the N-terminal side are shown in purple (c-ions).
Figure 5:
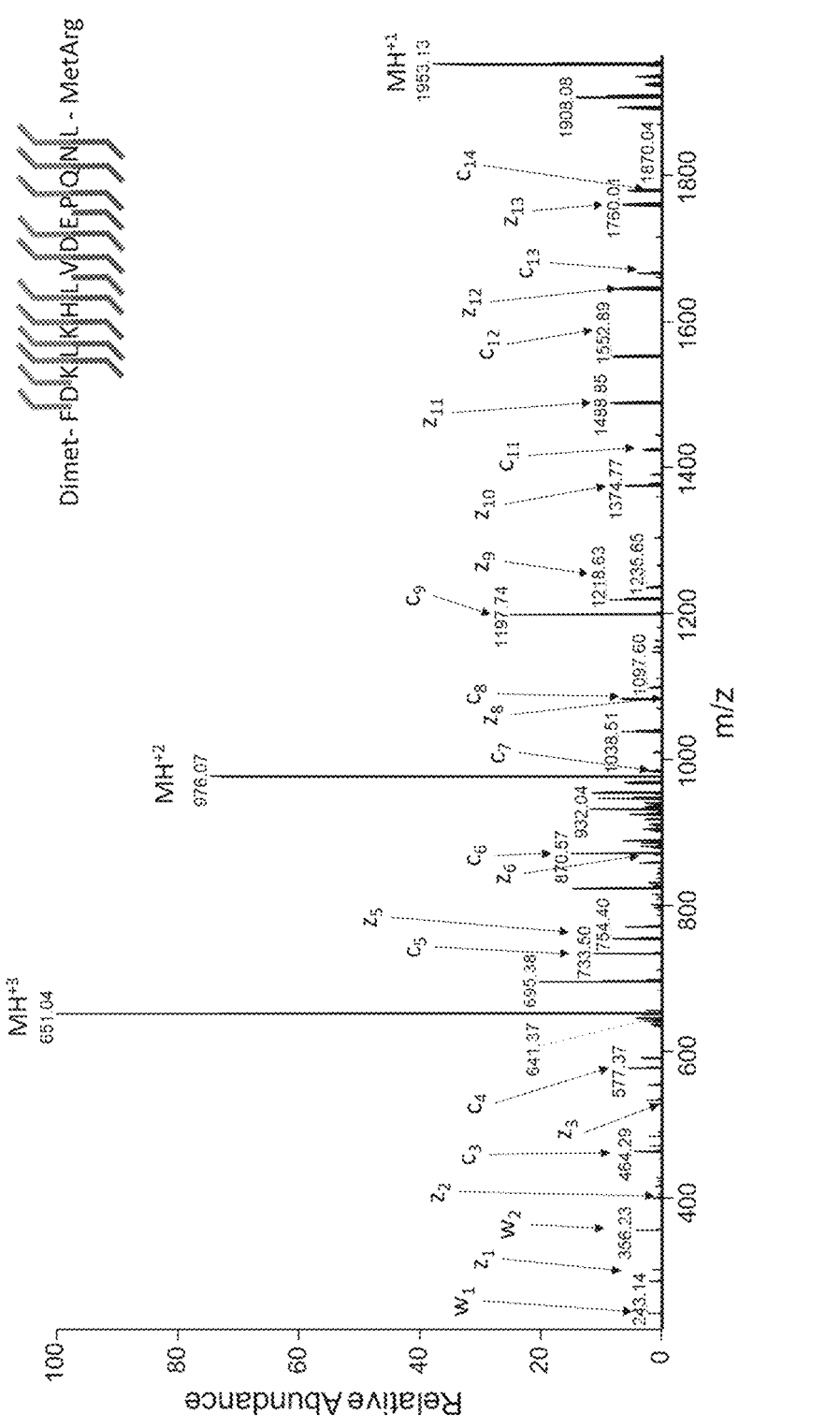
FIG. 5 illustrates a EThcD MS/MS spectra of the same peptide as in FIG. 4 but additionally labelled at the C-terminal with Arginine methyl ester ("MetArg"), i.e., dimethyl-FDKLKHLVDEPQNLX, SEQ ID NO: 18, where X is Arginine methyl ester). A better coverage of ions from the C-terminal side is observed across the overall sequence.
Figure 6:
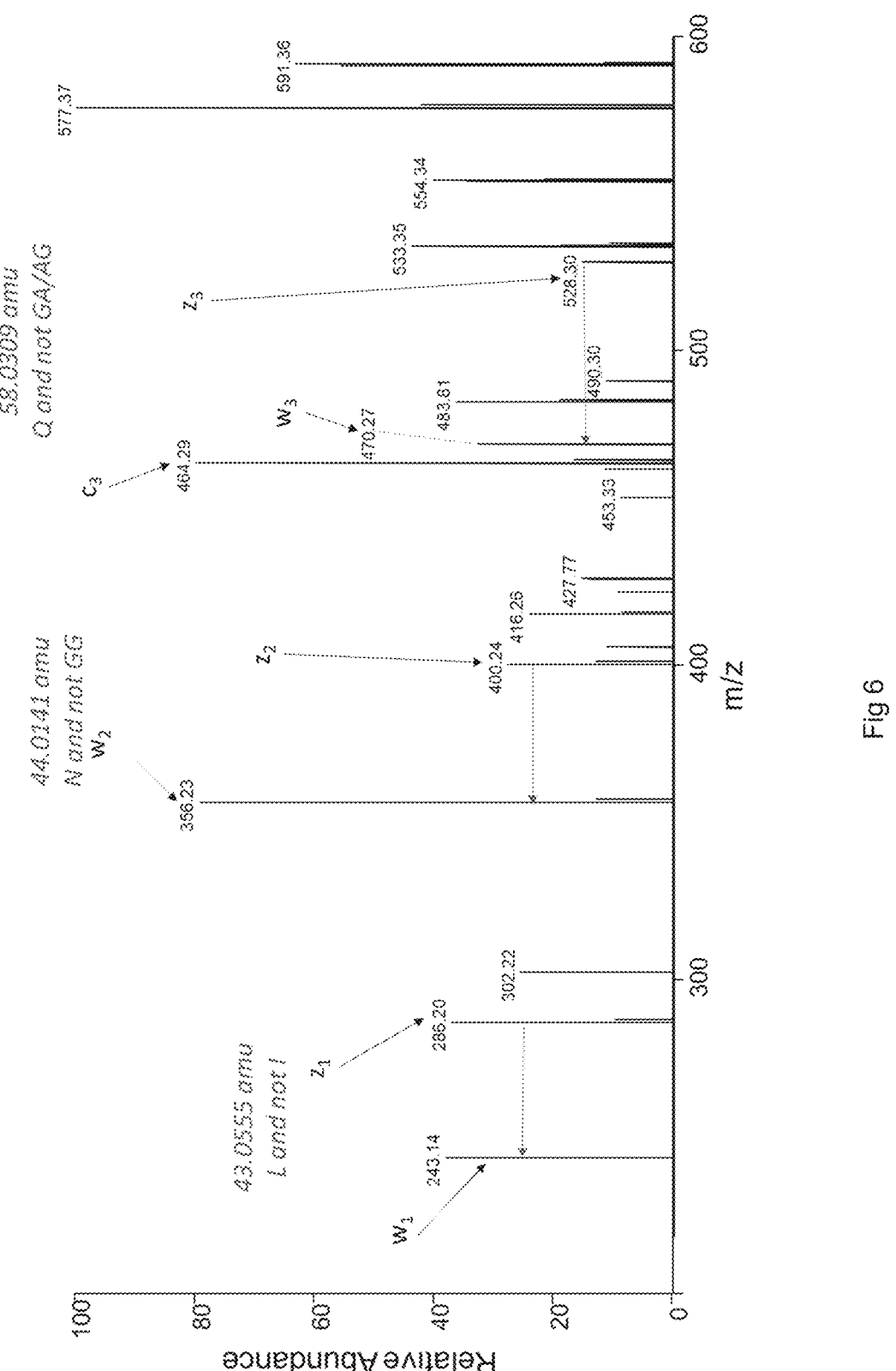
FIG. 6 illustrates a magnification of the 100 to 600 amu scale of FIG. 5 in order to illustrate experimentally the resolution of 3 different isobaric ambiguities. The $z_1->w_1$ ion with a mass shift of 43.055 amu allows identifying a Leucine at the C-terminal side of the peptide (instead of an isoleucine) while the $z_2->w_2$ with a mass shift of 44.0141 amu allows resolving the presence of Asparagine over GG in the penultimate C-terminal end and finally $z_3$ to $w_3$ with a mass shift of 58.0309 amu allows confirming the presence of glutamine over the 2 residues alanine and glycine in $3^{rd}$ position from the C-terminal. The red arrow illustrates the paired z to w transition.
Figure 7A:
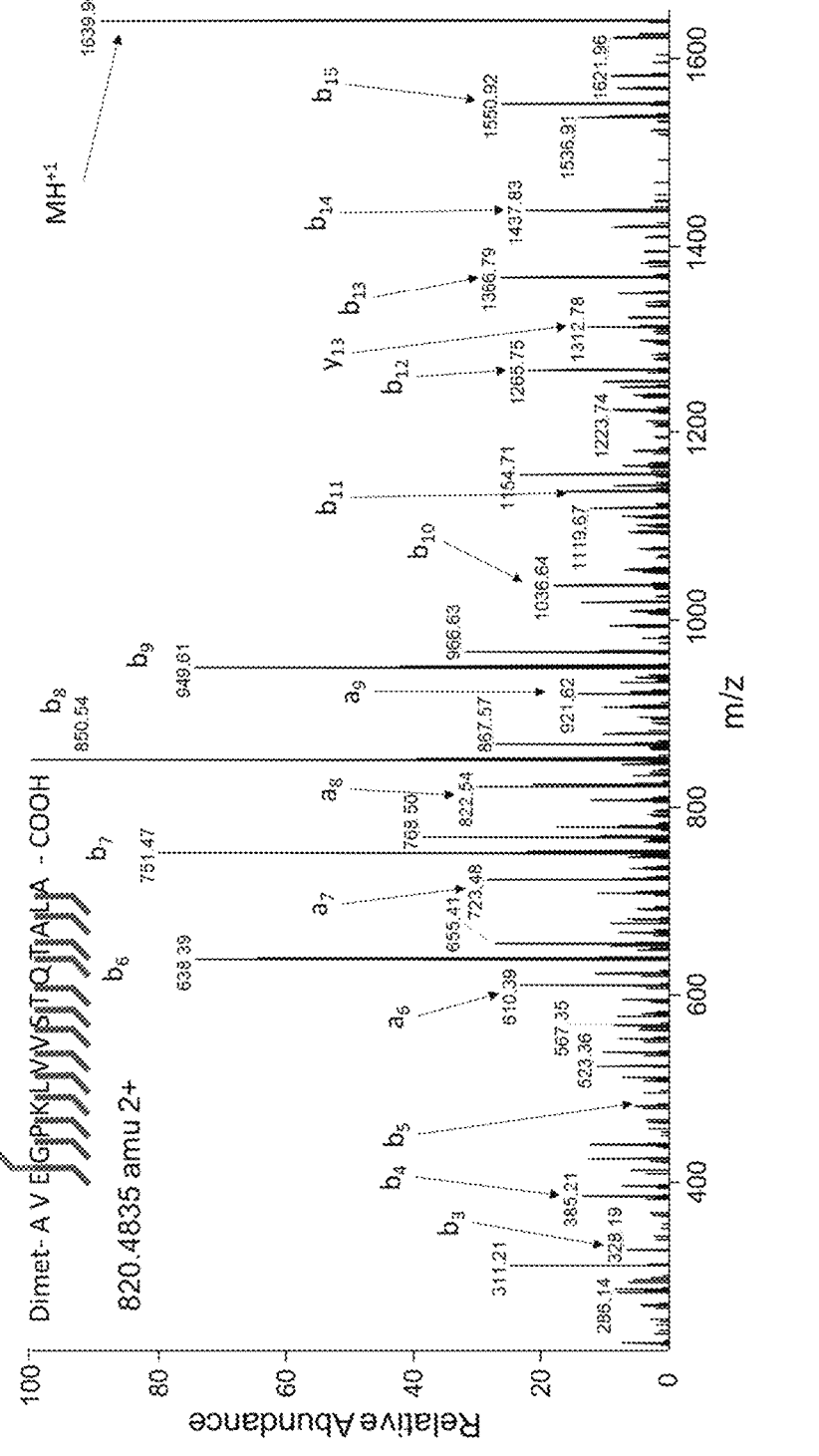
In FIG. 7a, dimethyl-AVEGPKLVVSTQTALA (SEQ ID NO: 2) is shown; whereas in FIG. 7d, dimethyl-AVEG-PKLVVSTQTALAX where X is Arginine methyl ester (SEQ ID NO: 11) is shown.
Figure 7B:
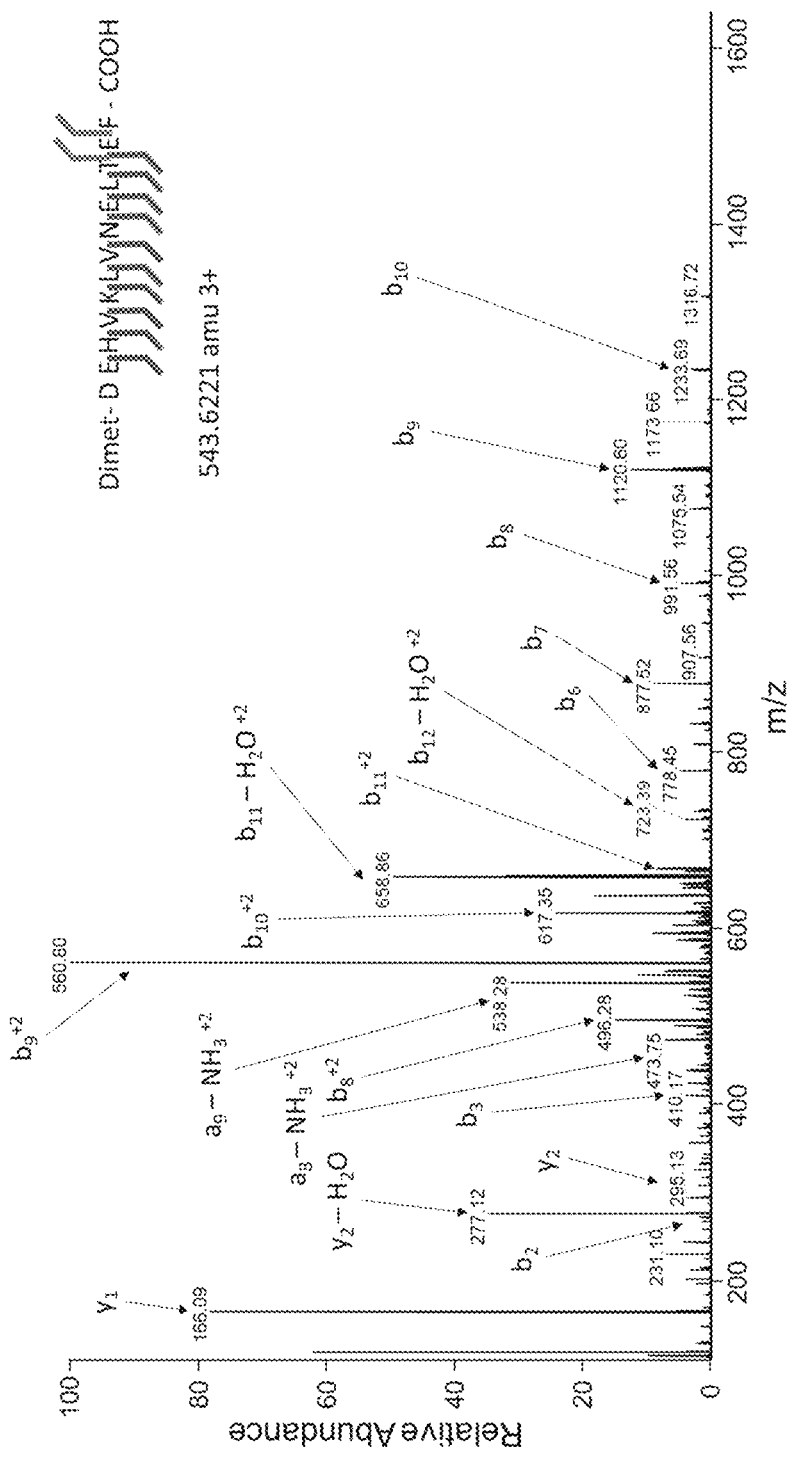
In FIG. 7b, dimethyl-DE-HVKLVNELTEF (SEQ ID NO: 3) is shown; whereas in FIG. 7e, dimethyl-DEHVKLVNELTEFX where X is Arginine methyl ester (SEQ ID NO: 12) is shown.
Figure 7C:
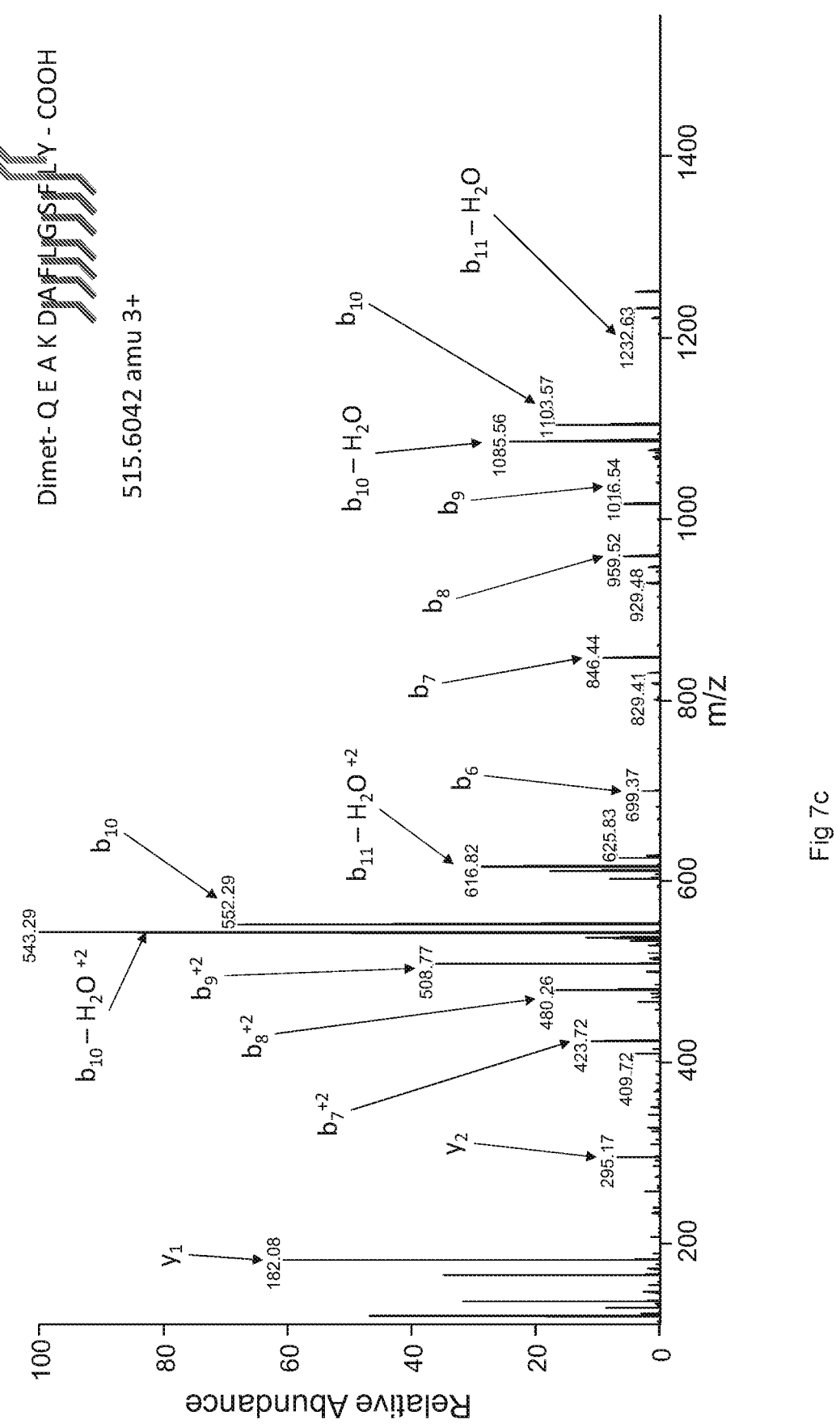
In FIG. 7c, dimethyl-QEAKDAFLGSFLY (SEQ ID NO: 4) is shown; whereas in FIG. 7f, dimethyl-QEAKDAFLGSFLYX where X is Arginine methyl ester (SEQ ID NO: 13) is shown.
Figure 7D:
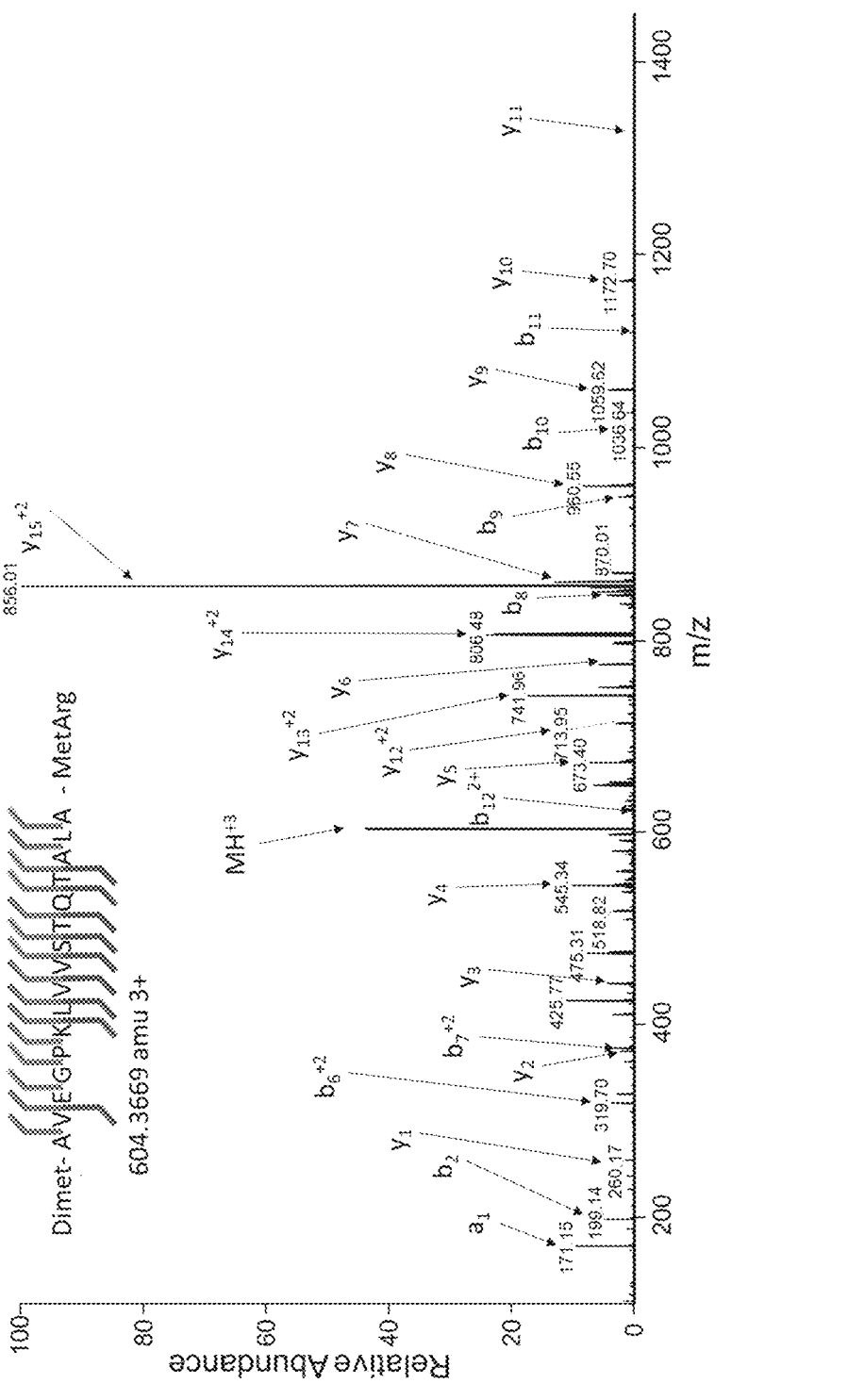
FIG. 7 illustrates 3 different peptides resulting from the chymotrypsin digestion of BSA, all dimethylated at the N-terminal and Lysine residue side-chain only (3 spectra on the left). The same peptides were also labelled at the C-terminal end with MetArg (three spectra on the right). The analysis was performed in HCD mode. Additionally, the labelling was performed on-column (Evosep tip) and loaded directly on the Mass spectrometer. The comparison illustrates the better coverage of the generated C-terminal ions (visualized by the red line presented in each sequence).
Figure 7E:
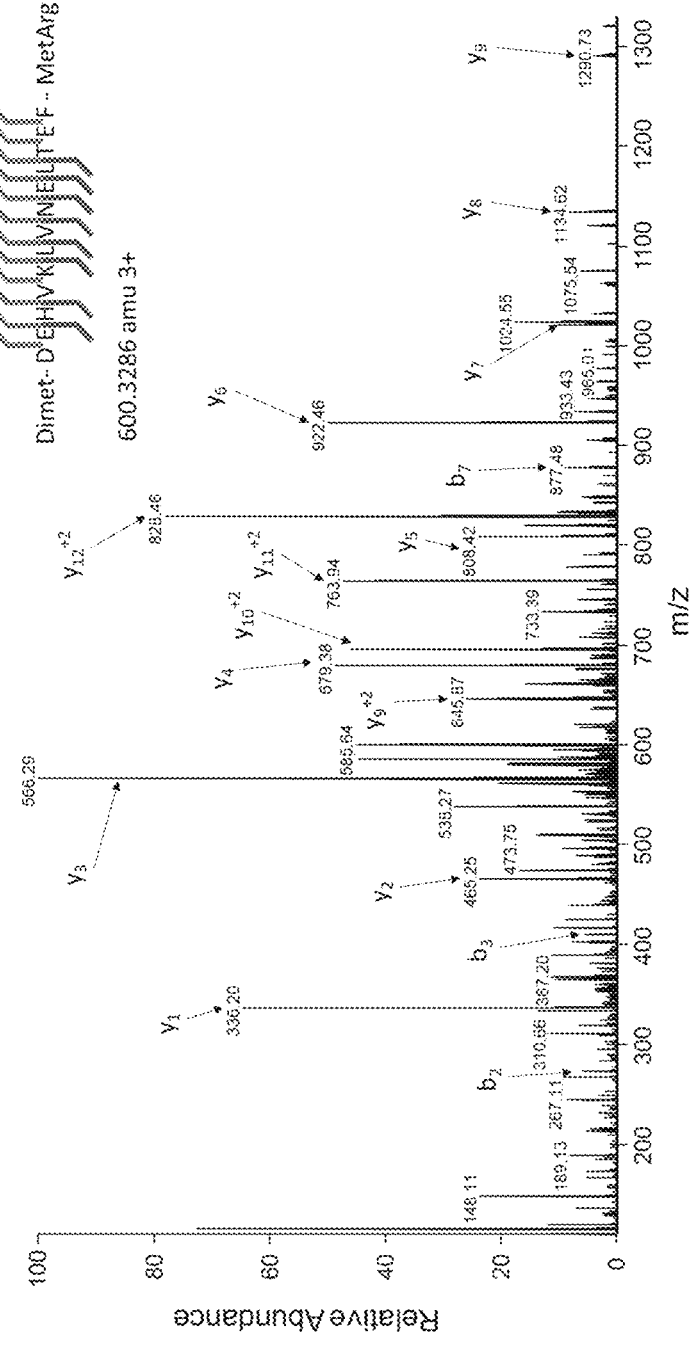
Figure 7F:
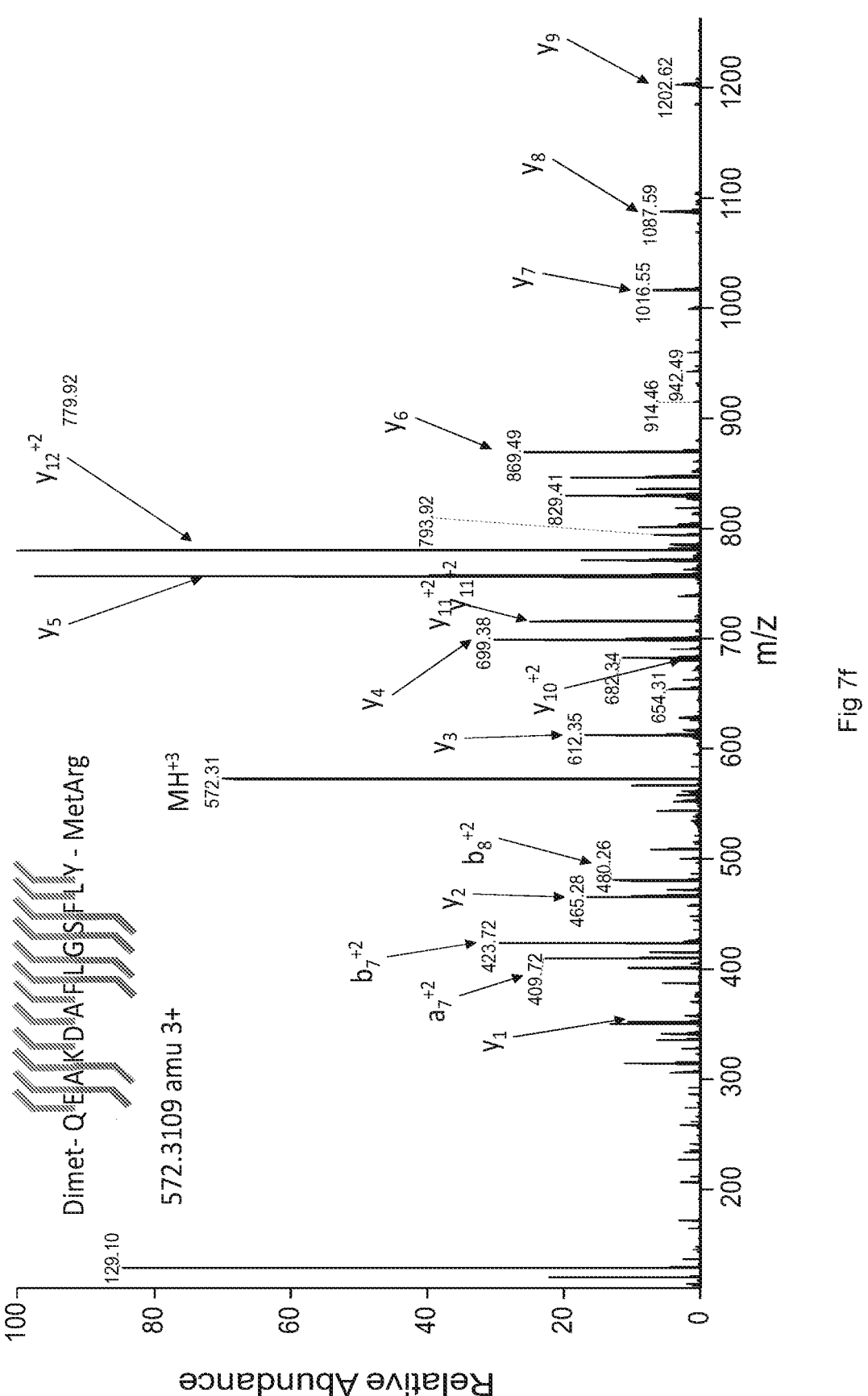

The inventors carried out an MS/MS analysis of the same peptide (non-labelled at the C-terminal and labelled at the C-terminal with Arginine methyl ester, FIGS. 4 and 5 respectively). The data were acquired on an Orbitral fusion in EThcD mode (Thermo-Fisher) instrument. The data shown in FIGS. 4, 5 and 6 illustrate the effect of the labelling on the ionization quality of peptide C-terminal fragments. The peptide sequence is a peptide from Bovine Serum Albumin resulting from the protease digestion with pepsin: FDKLKHLVDEPQNL (SEQ ID NO: 1) In FIG. 4, the peptide has been only dimethylated at the N-terminal and lysine. The peptide is a 2+ at 890.51 amu.

For the non C-terminal labelled form shown in FIG. 4, there are no observed short C-terminal fragments in the MS/MS spectra", only $z_{11}$, $z_{12}$ and $z_{13}$ were detected, and a few c ions were as well detected from ($c_6$ to $c_{13}$). Several forms of the same peptide were also found as 3+ and 4+ showing similar patterns of fragmentation (data not shown). Still in this FIG. 4, although pepsin cut at the C-terminal side of a leucine, no $z_1$ or $w_1$ ions are detectable to identify without any doubt this Leucine at the C-terminal end of the peptide. The same peptide after labelling with MetArg is shown in FIG. 5. The chosen spectrum is a 3+ of the peptide with C-terminal labelled with Arginine methyl ester at 650.71 amu (in addition the peptide was as well labelled like in FIG. 4 with dimethylation at the N-terminal and lysine). A more complete C-terminus fragmentation pattern and a more extended series of fragments from $z_1$ to $z_3$ $z_5$, $z_6$, $z_8$-$z_{13}$ are detectable, which allows for a better confirmation of the sequence content. FIG. 6 is a magnification of the range between 100 to 600 amu of FIG. 5 highlighting the specific ions $z_1$, $z_2$ and $z_3$ and their associated $w_1$, $w_2$ and $w_3$ ions respectively. This short sequence allows resolving 3 different isobaric situations. The ion $w_1$ at 243.1438 amu is 43.0555 amu from the $z_1$ ion thus confirming the presence of a Leucine at the C-terminal end of that peptide (instead of an Isoleucine). In a similar way, $w_2$ at 44.0141 amu of $z_2$ confirms the presence of N (instead of GG) and finally the $w_3$ at a lower mass of 58.0309 amu from $z_3$ confirms the presence of a Q instead of AG/GA sequence. Resolving those isobaric cases would not have been possible without C-terminal labelling.

FIG. 7 illustrates MS/MS spectra acquired in HCD mode for the following 3 peptides:

AVEGPKLVVSTQTALA (SEQ ID NO: 2); Dimethylated on peptide N-terminal end and Lysine (upper left figure) and the same peptide labelled at the C-terminal end with Arginine methyl ester (MetArg) (upper right figure).

DEHVKLVNELTEF (SEQ ID NO: 3); Dimethylated on peptide N-terminal end and Lysine (middle left figure) and the same peptide labelled at the C-terminal end with MetArg (middle right figure).

QEAKDAFLGSFLY (SEQ ID NO: 4); Dimethylated on peptide N-terminal end and Lysine (bottom left figure) and the same peptide labelled at the C-terminal end with MetArg (bottom right figure).

The peptides were from a chymotrypsin digestion of BSA following a labelling on-column (Evosep) according to the procedure detailed in example 4. All of the 3 peptides showed a better coverage of C-terminal y-ion with C-terminal label with MetArg (the 3 spectra on the right, shown by the red lines present in the sequence which are associated to detected fragments).

Figure 8:
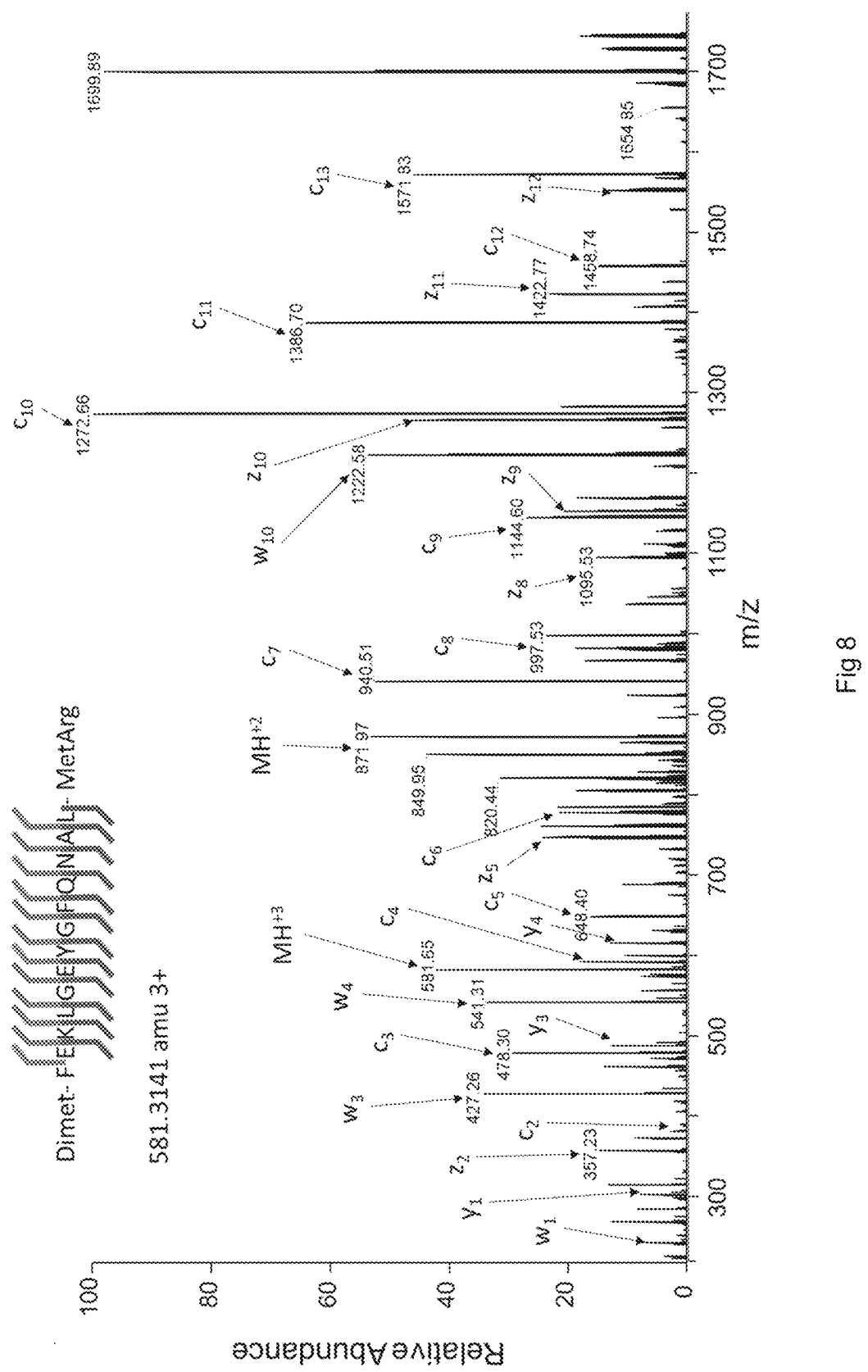
FIG. 8 illustrates EThcD MS/MS spectra of the peptide FEKLGEYGFQNAL (SEQ ID NO: 5) labelled at the C terminus with MetArg, i.e., dimethyl-FEKLGEYGFQNALX where X is Arginine methyl ester (SEQ ID NO: 14). A good coverage of ions from the C terminus is observed. Leucine L in position 1 from the C-terminal is identified from the generated w ions.
Figure 9:
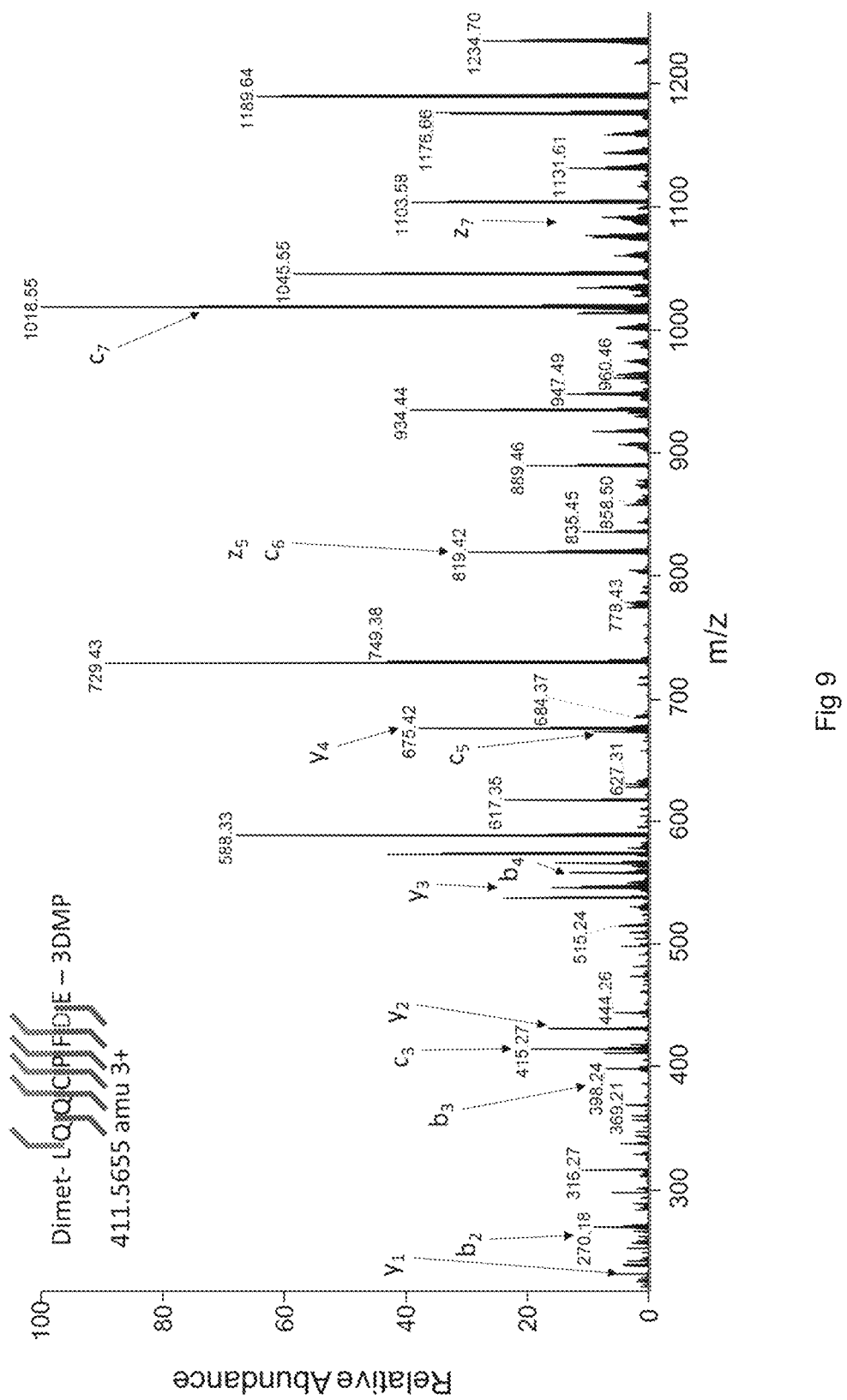
FIG. 9 illustrates EThcD MS/MS spectra of the labelled peptide LQQCPFDE (SEQ ID NO: 6) labelled with 3-DMP, i.e., dimethyl-LQQCPFDEX where X is 3-dimethylamino-1-propylamine (SEQ ID NO: 15). A good coverage of the sequence from the C terminal end is observed due to the C-terminal labelling, and the labelling of the D aspartic acid residue.

FIG. 8 illustrates MS/MS spectra acquired in EThcD mode for the following peptides:

FEKLGEYGFQNAL (SEQ ID NO: 5); as a 3+ ion at 581.31 amu. The spectra of sequence ID 5, also taken in EThcD mode after primary amine converted to dimethylation and C-terminal blocked with arginine methyl ester, shows a good coverage of C-terminal ions. The presence of a fragment ion at 286.2015 amu and a fragment ion at 243.1434 amu associated to z1 and w1 respectively confirm the presence of a leucine in z1 position. The non-labelled form of that peptide has no short z-ion fragment (data not shown). The last experimental spectrum (FIG. 9) is an example of the use of 3-DMP as a labelling reagent on the C-terminal side of the peptide LQQCPFDE (SEQ ID NO: 6).

The peptide was labelled first with dimethylation of all primary amine group and at the C-terminal and at the residues D with the reagent 3-DMP. Additionally, the cysteine was alkylated with iodoacetamide prior to pepsin digestion. The ion is a 3+ at 411.57 amu. Despite a poorer fragmentation pattern compared to the one observed with arginine methyl ester, labelling with 3-DMP generate few C-terminal fragments which were not observed in the non-labelled form of that similar peptide. It also highlights that Arginine as a C-terminal labelling reagent seems to generate more efficiently C-terminal fragment such as y,z ions.

Figure 12A:
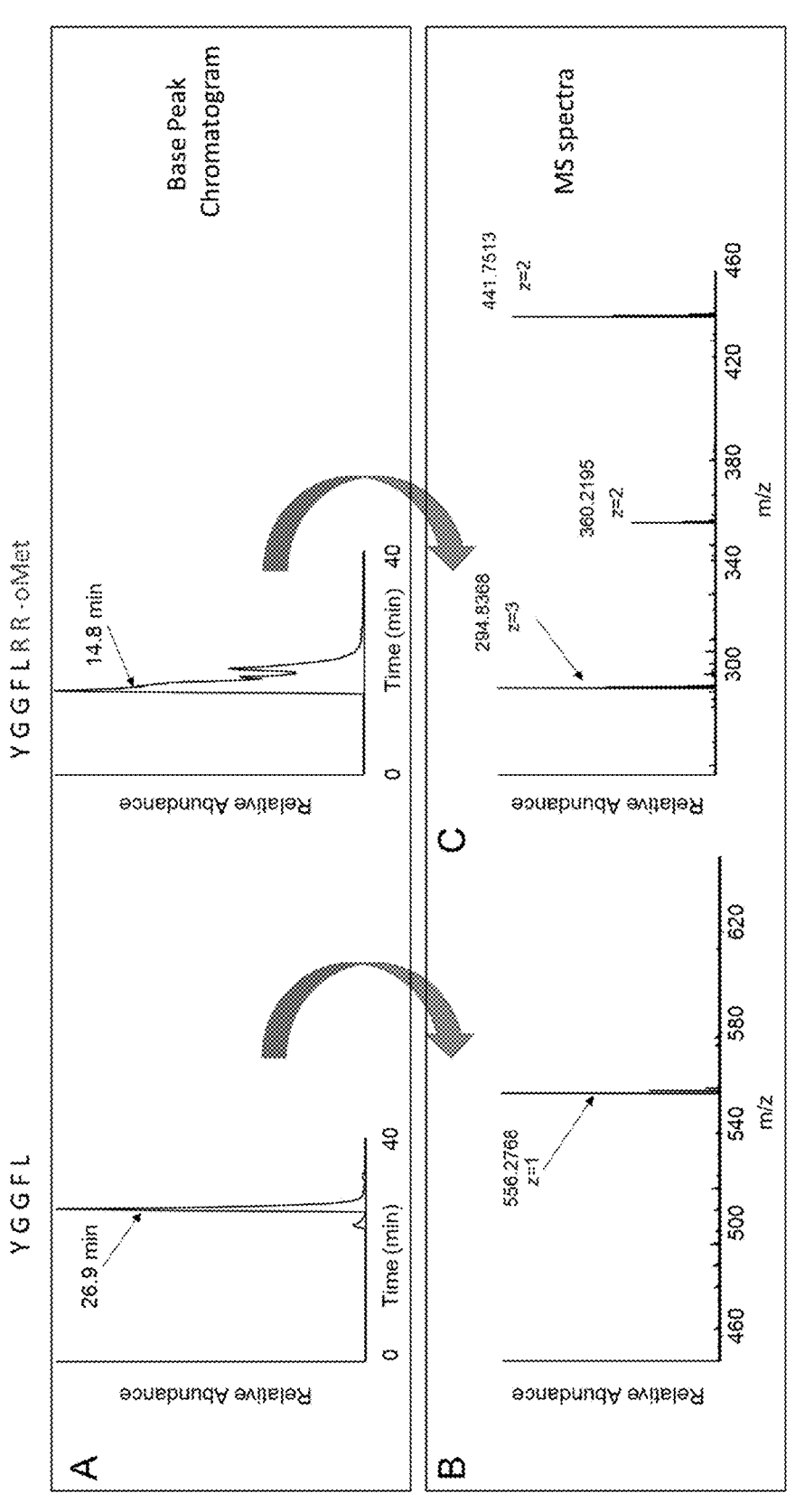
FIG. 12 illustrates MS spectra acquired in EThcD mode for the following peptide: YGGFL (SEQ ID NO: 7); as a 1+ ion at 556.2769 amu eluting at 26.9 min (FIG. 12B) or as labelled at the C-terminal end with arginine-arginine-methyl ester (YGGFLRR-omet, SEQ ID NO: 10) as a 2+ and 3+ ion at 441.7513 amu and 294.8368 amu respectively and eluting at 14.8 min (FIG. 12C). The MSMS spectra in EThcD of the 441,7513 amu peak shows a z3 ions at 442.3047 amu, then intense peak at 399.2480 amu correspond to a loss of 43.0567 amu which is a satellite w3 ion for a Leucine (w3 is LRR-met).
Figure 12B:
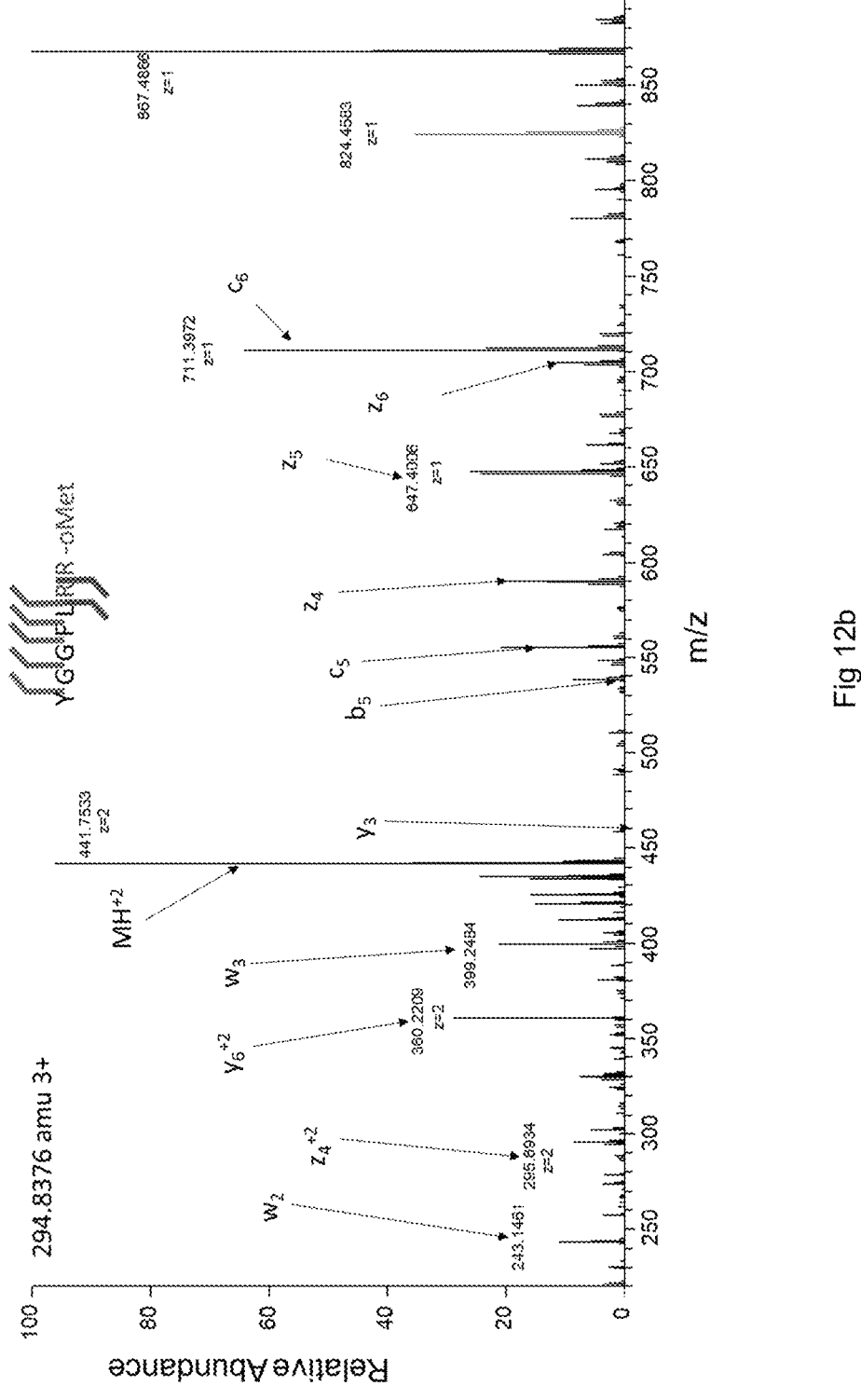

FIG. 12 illustrates MS spectra acquired in EThcD mode for the following peptide: YGGFL (SEQ ID NO: 7); as a 1+ ion at 556.2769 amu eluting at 26.9 min (FIG. 12B) or as labelled at the C-terminal end with arginine-arginine-methyl ester (YGGFLRRmet) as a 2+ and 3+ ion at 441.7513 amu and 294.8368 amu respectively and eluting at 14.8 min (FIG. 12C). The MSMS spectra in EThcD of the 441,7513 amu peak shows a z3 ions at 442.3047 amu, then intense peak at 399.2480 amu correspond to a lost of 43.0567 amu which is a satellite w3 ion for a Leucine (w3 is LRR-met). Adding the RR-omet reduce drastically the peptide retention time from 26.9 min to 14.8 min which can be a useful strategy to detect very hydrophobic peptides.

One or more currently preferred embodiments have been described by way of example. It will be apparent to persons skilled in the art that a number of variations and modifications can be made without departing from the scope of the invention as defined in the claims.

The Sequence Listing is being submitted electronically in ASCII format and is hereby incorporated by reference in its entirety. Said ASCII copy, created on May 27, 2022, is named 135583_000641_ST25.txt and is 8,192 bytes in size. No new matter is being introduced.

REFERENCES

Al-Warhi T I, Al-Hazimi H M A, El-Faham A (2012) Recent development in peptide coupling reagents. Journal of Saudi Chemical Society 16, 97-116. doi:10.1016/j.jscs.2010.12.006.

Armirotti A, Millo E, Damonte G. (2007) How to Discriminate Between Leucine and Isoleucine by Low Energy ESI-TRAP MSn, J. Am. Soc. Mass Spectrom., 18, 57-63.

Breddam K, Widmer F, Johansen JT (1980) Carboxypeptidase Y catalyzed transpeptidations and enzymatic peptide synthesis, Carlsberg Res. Commun 45, 237-247.

Falick A M, Hines W M, Medzihradszky K F, Baldwin M A, Gibson B W. (1993) Low-Mass Ions Produced from Peptides by High-Energy Collision-Induced Dissociation in Tandem Mass Spectrometry. J. Am. Soc. Mass Spectrom., 4(11), 882-893.

Frese C K, Altelaar A F, van den Toorn H, Nolting D, Griep-Raming J, Heck A J, Mohammed S. (2012) Toward full peptide sequence coverage by dual fragmentation combining electron-transfer and higher-energy collision dissociation tandem mass spectrometry. *Anal Chem.;* 84(22):9668-73. doi: 10.1021/ac3025366. Epub 2012 Oct. 31.

Frey B L, Ladror D T, Sondalle S B, Krusemark C J, Jue A L, Coon J J, Smith L M. (2013), Chemical derivatization of peptide carboxyl groups for highly efficient electron transfer dissociation. J Am Soc Mass Spectrom; 24(11): 1710-21. doi: 10.1007/s13361-013-0701-2.

Goodlett D R, Keller A, Watts J D, Newitt R, Yi E C, Purvine S, Eng J K, von Haller P, Aebersold R, Kolker E. (2001) Differential stable isotope labeling of peptides for quantitation and de novo sequence derivation. Rapid Commun. Mass Spectrom.; 15: 1214-1221 DOI:10.1002/rcm.362.

Johnson R S, Martin S A, Biemann K. (1988) Collision-induced fragmentation of (M+H)+ ions of peptides. Side chain specific sequence ions. International Journal of Mass Spectrometry and Ion Processes. https://doi.org/10.1016/0168-1176(88)80060-0.

Kjeldsen F, Haselmann K F, Sørensen E S, Zubarev R A. (2003) Distinguishing of Ile/Leu amino acid residues in the PP3 protein by (hot) electron capture dissociation in Fourier transform ion cyclotron resonance mass spectrometry. Anal Chem.; 75(6):1267-74.

Ko B J & Brodbelt J S (2012) Enhanced Electron transfer Dissociation of peptides modified at C-terminus with fixed charges. J. Am. Mass Spectrom 23:1991-2000. Doi: 10.1007/s13361-012-0458-z.

Kovalyov S V, Zhokhov S S, Onoprienko L V, Vaskovsky B V, Lebedev A T. (2017) Exploration of doubtful cases of leucine and isoleucine discrimination in mass spectrometric peptide sequencing by electron-transfer and higher-energy collision dissociation-based method. Eur J Mass Spectrom (Chichester).; 23(6):376-384. doi: 10.1177/1469066717730705.

Krishna P, Prabhakar S, Vairamani M. (1998) Differentiation of derivatized Leucine and Isoleucine by tandem Mass spectrometry under Liquid secondary Ion Mass spectral condition. Rapid Commun Mass Spectrom 12. 1429-1434.

Krusemark C J, Frey B L, Smith L M, Belshaw P J. (2011) Complete chemical modification of amine and acid functional groups of peptides and small proteins. *Methods Mol Biol.;* 753:77-91. doi: 10.1007/978-1-61779-148-2_6.

Lebedev A T, Damoc E, Makarov A A, Samgina T Y (2014) Discrimination of Leucine and Isoleucine in Peptides Sequencing with Orbitrap Fusion Mass Spectrometer. Anal. Chem. 2014, 86, 7017-7022 dx.doi.org/10.1021/ac501200h.

Lindh I, Hjelmqvist L, Bergman T, Sjövall J, Griffiths WJ. (2000) De novo sequencing of proteolytic peptides by a combination of C-terminal derivatization and nano-electrospray/collision-induced dissociation mass spectrometry.

Journal of the American Society for Mass Spectrometry 11(8), 673-686 https://doi.org/10.1016/S1044-0305(00)00138-0.

Oh H B, Moon B. (2015) Radical-driven peptide backbone dissociation tandem mass spectrometry. Mass Spectrom Rev.; 34(2):116-32. doi: 10.1002/mas.21426.

Ma B. (2015) Novor: real-time peptide de novo sequencing software. J Am. Soc of Mass Spectrom. 26(11) 1885-1894.

Ma M, Kutz-Naber K K, Li L. (2007) Methyl esterification assisted MALDI FTMS characterization of the Orcokinin Neuropeptide family. Anal. Chem, 79 673-681.

Medzihradszky K F & Chalkley R J. (2016) Lesson I De novo peptide sequencing by Tandem Mass spectrometry, Mass Spectrum. Rev.; 34(1): 43-63.

Mirzaei H and Regnier F. (2006) Enhancing Electrospray Ionization Efficiency of Peptides by Derivatization. Anal. Chem. 78, 12, 4175-4183 DOI: 10.1021/ac0602266.

Nakamura T, Nagaki H, Ohki Y, Kinoshita T. (1990) Differentiation of Leucine and Isoleucine Residues in Peptides by Consecutive Reaction Mass Spectrometry. Anal. Chem., 62(3), 311-313.

Perkins, P. D., Fischer, S. M. (2010) Peptide Derivatization method to increase fragmentation information from MS/MS spectra. Patent publication no US 2010/7,838,303 B2

Ramsay S L, Steinborner S T, Waugh R J, Dua S, Bowie J H A. (1995) Simple Method for Differentiating Leu and Ile in Peptides. The Negative-Ion Mass Spectra of [M H] Ions of Phenylthiohydantoin Leu and Ile. Rapid Commun. Mass Spectrom., 9(13), 1241-1243.

Riley N M & Coon J J (2018) The role of Electron transfer Dissociation in Modern Proteomics. Anal. Chem. 90, 40-64. doi: 10.1021/acs.analchem.7b04810

Wysocki V H, Resing K A, Zhang Q, Cheng G. (2005) Mass spectrometry of peptides and proteins. Methods.; 35(3): 211-22. Epub 2005 Jan. 20. Review.

Xiao Y, Vecchi M M, Wen D. (2016) Distinguishing between Leucine and Isoleucine by Integrated LC-MS Analysis Using an Orbitrap Fusion Mass Spectrometer. Anal Chem. 2016 Nov. 1; 88(21):10757-10766. Epub 2016 Oct. 14.

Xu G, Shin S B Y, Jaffrey S R. (2011) ACS Chem Biol; 6(10), 1015-1020. Doi:10.1021/cb200164h.

Zhokhov S S, Kovalyov S V, Samgina T Y, Lebedev A T. (2017) An EThcD-Based Method for Discrimination of Leucine and Isoleucine Residues in Tryptic Peptides. J Am Soc Mass Spectrom; 28(8):1600-1611. doi: 10.1007/s13361-017-1674-3. Epub 2017 Apr. 26.

What is claimed is:

1. A method for distinguishing isobaric amino acids and amino acid combinations of isoleucine and leucine; asparagine and glycine-glycine; glutamine and glycine-alanine; and/or glutamine and alanine-glycine, during polypeptide sequencing, the method comprising:

obtaining a peptide of interest and/or digesting a polypeptide of interest with a protease to produce shorter peptides, wherein the protease is pepsin, asp-N, chymotrypsin, thermolysin, or Lys-N;

reacting the obtained and/or generated peptides with a coupling reagent capable of derivatizing the free C-terminal carboxylic acid function of the peptides, under conditions to add a basic functional group having a positive charge;

selecting a charge state of 2+ or more, and fragmenting the derivatized peptides in a mass spectrometer under conditions effective to generate at least w ions; and detecting said w ions by mass spectrometry, and identifying derivatized peptides which incorporate the additional mass of said basic functional group;

wherein positive charges are added to the free C-terminal carboxylic acid function of the peptide and/or polypeptide, and said w ions are analyzed to distinguish between the isobaric amino acids and amino acid combinations of: isoleucine and leucine; asparagine and glycine-glycine; glutamine and glycine-alanine; and/or glutamine and alanine-glycine.

2. The method of claim 1, wherein the reacting step comprises chemical or enzymatic coupling of said basic functional group to the polypeptide's C-terminal end.

3. The method of claim 1, wherein the coupling reagent is a carbodiimide.

4. The method of claim 3, wherein the carbodiimide is 1-ethyl-3-(3-dimethylaminopropyl) carbodiimide (EDC).

5. The method of claim 1, wherein the coupling reagent is a phosphonium ion.

6. The method of claim 5, wherein the phosphonium ion is (7-Azabenzotriazol-1yloxy)tripyrrolidinophosphonium hexafluorophosphate (PyAOP).

7. The method of claim 1, wherein the basic functional group added to the obtained and/or generated peptides comprises a secondary, tertiary or quaternary amine, a phosphonium or a sulfonium ion.

8. The method of claim 7, wherein the basic functional group added to the obtained and/or generated peptides is 3-dimethylamino-1-propylamine (3-DMP) or arginine methyl ester (MetArg) or a dipeptide Arginine-arginine-methyl ester (R-R-omet).

9. The method of claim 1, wherein an additive is used together with the coupling reagent in said reacting step.

10. The method of claim 9, wherein the additive is ethyl cyano(hydroxyimino)acetate (OXYMA).

11. The method of claim 1, further comprising a step of modifying lysine residues on the obtained and/or generated peptides.

12. The method of claim 11, wherein the lysine residues are blocked by guanidisation using O-methylisourea under conditions effective to derivatize said lysine groups with homoarginine groups or dimethylated using formaldehyde.

13. The method of claim 1, further comprising a step of derivatizing the free amino group at the N-terminus of the obtained and/or generated peptides.

14. The method of claim 13, wherein the free amino group at the N-terminus of the polypeptide is derivatized with homoarginine groups or dimethylated using formaldehyde.

15. The method of claim 1, wherein the obtained and/or generated peptides and/or said derivatized peptides are cleaned using a chromatography column or liquid phase separation.

16. The method of claim 1, wherein the obtained and/or generated peptides and/or said derivatized peptides are cleaned by solid-phase extraction (SPE), using reverse phase, normal phase or ion exchange SPE.

17. The method of claim 1, wherein the obtained and/or generated peptides and/or said derivatized peptides are cleaned by liquid phase separation using water saturated ethyl acetate, and dried using a concentrator under low pressure.

18. The method of claim 8, wherein the C-terminal carboxylic acid function of the peptides has an additional mass of 170.116761 Da (4N 7C 14H 1O), due to MetArg coupling.

19. A method for distinguishing isobaric amino acids and amino acid combinations of isoleucine and leucine; asparagine and glycine-glycine; glutamine and glycine-alanine; and/or glutamine and alanine-glycine, during polypeptide sequencing, the method comprising:

digesting a polypeptide of interest with a plurality of proteases to produce shorter peptides, wherein the plurality of proteases is two or more of pepsin, asp-N, chymotrypsin, thermolysin, and Lys-N;

reacting the produced peptides with a coupling reagent capable of derivatizing the free C-terminal carboxylic acid function of the peptides, under conditions to add a basic functional group having a positive charge;

selecting a charge state of 2+ or more, and fragmenting the derivatized peptides in a mass spectrometer under conditions effective to generate at least w ions; and detecting said w ions by mass spectrometry, and identifying derivatized peptides which incorporate the additional mass of said basic functional group;

wherein positive charges are added to the free C-terminal carboxylic acid function of the peptide and/or polypeptide, and said w ions are analyzed to distinguish between the isobaric amino acids and amino acid combinations of: isoleucine and leucine; asparagine and glycine-glycine; glutamine and glycine-alanine; and/or glutamine and alanine-glycine; and wherein said method achieves complete polypeptide sequencing while resolving all amino acid ambiguities.

20. The method of claim 19, wherein the plurality of proteases comprises a combination of pepsin and chymotrypsin.

* * * * *